US009629382B2

(12) United States Patent
Yamka et al.

(10) Patent No.: US 9,629,382 B2
(45) Date of Patent: Apr. 25, 2017

(54) COMPOSITIONS AND METHODS FOR TREATING OSTEOARTHRITIS

(75) Inventors: Ryan Michael Yamka, Topeka, KS (US); Nolan Zebulon Frantz, Meadville, PA (US); Xiangming Gao, Topeka, KS (US); Samer Al-Murrani, Topeka, KS (US)

(73) Assignee: Hill's Pet Nutrition, Inc., Topeka, KS (US)

( * ) Notice: Subject to any disclaimer, the term of this patent is extended or adjusted under 35 U.S.C. 154(b) by 507 days.

(21) Appl. No.: 13/054,745

(22) PCT Filed: Jul. 20, 2009

(86) PCT No.: PCT/US2009/051169
§ 371 (c)(1),
(2), (4) Date: Apr. 13, 2011

(87) PCT Pub. No.: WO2010/009474
PCT Pub. Date: Jan. 21, 2010

(65) Prior Publication Data
US 2011/0183006 A1 Jul. 28, 2011

Related U.S. Application Data

(60) Provisional application No. 61/082,185, filed on Jul. 18, 2008.

(51) Int. Cl.
| | | |
|---|---|---|
| *A01N 59/26* | (2006.01) |
| *A23K 50/40* | (2016.01) |
| *A61K 31/01* | (2006.01) |
| *A61K 31/202* | (2006.01) |
| *A61K 31/726* | (2006.01) |
| *A61K 45/06* | (2006.01) |
| *A23K 20/174* | (2016.01) |
| *A23K 20/158* | (2016.01) |
| *A23K 20/20* | (2016.01) |
| *A23L 33/10* | (2016.01) |
| *A23L 33/12* | (2016.01) |
| *A23L 33/15* | (2016.01) |
| *A23L 33/16* | (2016.01) |
| *A23L 33/175* | (2016.01) |

(52) U.S. Cl.
CPC ............ *A23K 50/40* (2016.05); *A23K 20/158* (2016.05); *A23K 20/174* (2016.05); *A23K 20/30* (2016.05); *A23L 33/10* (2016.08); *A23L 33/12* (2016.08); *A23L 33/15* (2016.08); *A23L 33/16* (2016.08); *A23L 33/175* (2016.08); *A61K 31/01* (2013.01); *A61K 31/202* (2013.01); *A61K 31/726* (2013.01); *A61K 45/06* (2013.01)

(58) Field of Classification Search
CPC .... A61K 31/01; A61K 31/202; A61K 31/726; A61K 45/06; A61K 2300/00; A61K 31/31; A23K 1/1603; A23K 1/164; A23K 1/1758; A23K 1/1846; A23K 50/40; A23K 20/30; A23K 20/158; A23K 20/174; A23L 1/30; A23L 1/302; A23L 1/304; A23L 1/3051; A23L 1/3008
See application file for complete search history.

(56) References Cited

U.S. PATENT DOCUMENTS

| | | | |
|---|---|---|---|
| 6,277,842 B1 * | 8/2001 | Carthron ..................... 514/188 |
| 8,633,246 B2 | 1/2014 | Fritsch |
| 8,633,247 B2 | 1/2014 | Caterson et al. |
| 2002/0099032 A1 * | 7/2002 | Higashi et al. ................ 514/62 |
| 2006/0073192 A1 | 4/2006 | Friesen et al. |
| 2011/0183006 A1 | 7/2011 | Yamka et al. |

FOREIGN PATENT DOCUMENTS

| | | | |
|---|---|---|---|
| JP | 2000-053569 | * | 2/2000 |
| WO | WO 0041566 | | 7/2000 |
| WO | WO 2006/002976 | | 1/2006 |
| WO | 2006/053010 | * | 5/2006 |
| WO | WO 2006/053010 | | 5/2006 |
| WO | WO 2007/002837 | | 1/2007 |
| WO | WO 2007/079301 | | 7/2007 |

OTHER PUBLICATIONS

JP 2000-053569 English language translation of above JP document.*
Frantz et al., "Identification of gene changes in geriatric dogs fed a test or control food," FASEB Journal, vol. 21, No. 6, Apr. 2007, XP002546604, abstract only.
International Search Report and Written Opinion for International Appln. No. PCT/US2009/051169 dated Sep. 21, 2009.
Mateescu et al., "Increased MIG-6 mRNA transcripts in osteoarthritic cartilage," Biochemical and Biophysical Research Communications 332 (2005) 482-486.
Alturfan et al., 2007, "Increased Serum Sialic Acid Levels in Primary Osteoarthritis and Inactive Rheumatoid Arthritis," Tohoku J. Exp. Med. 213(3):241-248.
Gregory et al., 2008, "Dietary Supplements for Osteoarthritis," American Family Physician 77(2):177-184.
Shikhman et al., 2005, "Chondroprotective Activity of N-Acetylglucosamine in Rabbits with Experimental Osteoarthritis," Ann. Rheum. Dis. 64(1):89-94.
Kim et al., 2005, "Increased interleukin-17 production via a phosphoinositide 3-kinase/Akt and nuclear factor κB-dependent pathway in patients with rheumatoid arthritis," Arthritis Res. Ther., 7:R139-R148.
Ruiz-Romero et al., 2008, "Proteomic analysis of human osteoarthritic chondrocytes reveals protein changes in stress and glycolysis," Proteomics, 8:495-507.
Tchetverikov et al., 2005, "MMP protein and activity levels in synovial fluid from patients with joint injury, inflammatory arthritis, and osteoarthritis," Ann. Rheum. Dis. 64:694-698.

(Continued)

*Primary Examiner* — Suzanne Ziska

(57) ABSTRACT

The present invention provides compositions and methods for treatment of abnormal conditions in a subject, wherein the abnormal condition affects the musculoskeletal joints of the subject.

6 Claims, 17 Drawing Sheets

(56) References Cited

OTHER PUBLICATIONS

Majeswka et al., Influence of Melatonin and its Precursor L-Tryptophan on Th1 Dependent Contact Hypersensivity, J. Phys & Phar. 2007, 58, Supp. 6, 125-132.
Valverde et al., Sugar-mediated transcriptional regulation of the Gap gene system and concerted photosystem II functional modulation in the microalga *Scenedesmus vacuolatus*, Planta 2005 221:937-952.

* cited by examiner

| Nutrient | Nutrient Guarantee % | As Fed % | Dry Matter % | As Fed, Caloric Basis g/100 kcal |
|---|---|---|---|---|
| Protein | 17.0 Minimum | 18.5 | 20.1 | 5.1 |
| Fat | 11.0 Minimum | 14.4 | 15.7 | 4.0 |
| Carbohydrate (NFE) | | 46.9 | 51.0 | 13.0 |
| Crude Fiber | 12.0 Maximum | 8.0 | 8.7 | 2.2 |
| | | | | mg/100 kcal$^3$ |
| Calcium | 0.45 Minimum | 0.64 | 0.70 | 177 |
| Phosphorus | 0.30 Minimum | 0.50 | 0.54 | 138 |
| Sodium | | 0.16 | 0.17 | 44 |
| Potassium | | 0.76 | 0.83 | 210 |
| Magnesium | | 0.128 | 0.139 | 35 |
| Carnitine | 200 ppm Minimum | 323 ppm | 351 ppm | 9 |
| Omega-3 Fatty Acids Total | 2.00 Minimum | 3.49 | 3.79 | 965 |
| Omega-6:Omega-3 Fatty Acid Ratio | | 0.7 : 1 | | |
| Omega-6 Fatty Acids Total | | 2.46 | 2.67 | 680.50 |
| Alpha-Linolenic Acid (ALA) | | 2.55 | 2.77 | 705.4 |

Figure 4

COMPOSITIONS AND METHODS FOR TREATING OSTEOARTHRITIS

CROSS-REFERENCE TO RELATED APPLICATIONS

This application is a national stage entry under 35 U.S.C. §371 of International Patent Application No. PCT/US2009/0051169, filed 20 Jul. 2009, which claims priority to U.S. Provisional Patent Application No. 61/082,185, filed on 18 Jul. 2008.

FIELD OF THE INVENTION

The invention relates to compositions and methods for treating abnormal joint conditions in an animal, wherein the abnormal joint condition involves the musculoskeletal joints of the animal. In particular, this invention relates to treatment of abnormal musculoskeletal joint conditions including osteoarthritis, rheumatoid arthritis and local joint inflammation and the relief of symptoms associated with such abnormal, musculoskeletal joint conditions. The application also encompasses modulating genes differentially expressed in animals, for example, genes differentially expressed in arthritic animals compared to non-arthritic animals, by administering a composition of the invention. The present invention also related to the identification of novel biomarkers in companion animals, including dogs and cats, diagnostic methods, compositions and kits related thereto.

BACKGROUND OF THE INVENTION

It is generally accepted in the scientific community that genes play a role in animal development and that the regulation of gene expression plays a key role in the development of some diseases or conditions that affect an animal's health and well being. Similarly, the differential expression of genes is one factor in the development of such diseases and conditions and the evaluation of gene expression patterns has become widely recognized as crucial to understanding the development and control of such diseases and conditions at the molecular level. To advance the understanding of genes and their relationship to disease, a number of methods have been developed for studying differential gene expression, e.g., DNA microarrays, expressed tag sequencing (EST), serial analysis of gene expression (SAGE), subtractive hybridization, subtractive cloning and differential display (DD) for mRNA, RNA-arbitrarily primed PCR (RAP-PCR), Representational Difference Analysis (RDA), two-dimensional gel electrophoresis, mass spectrometry, and protein microarray based antibody-binding for proteins.

Virtually all joints in the body of a mammal have cartilage. Cartilage is the supporting structure of the body and consists of thick bundles of fibrous protein (collagen) which are woven to form an articular surface. Proteoglycans fill extracellular spaces not occupied by collagen. Such proteoglycans are comprised of a combination of a protein and a sugar. Each proteoglycan subunit contains a protein core consisting of long chains of modified sugars known as glycosaminoglycans (GAGs). Glucosamine is the single most important component and precursor for GAGs. Synthesis of collagen by the body is dependent upon GAG synthesis. Chondrocytes in the cartilage utilize glucosamine to produce N-acetylglucosamine (NAG) and glucuronic acid, which are utilized by the body to form hyaluron. Hyaluron confers a lubricating property to the joint of the animal's body.

Cartilage is important in the body of animals for providing flexibility, compressibility under pressure, cushion, tensile strength, range of motion and smoothness of movement within joints. Examples of joints having cartilage include fingers and toes, neck, knee, hip, shoulder and the like. Animals can suffer from a number of conditions where cartilage is degraded thereby bringing about a reduction in the joint's flexibility, compressibility and often times resulting in a generalized inflammation of the joint and/or tissue surrounding the joint and in some cases the development of conditions such as osteoarthritis and rheumatoid arthritis. Such animals then have significant loss of joint function and experience pain.

Arthritis is a musculoskeletal disorder. Osteoarthritis is the most common type of arthritis in animals and humans. Osteoarthritis is a degenerative joint disease commonly occurring in humans and companion animals and the disease is characterized by degenerative changes in the articular cartilage, with loss of proteoglycan and collagen and proliferation of new bone formation at articular margins. These changes are accompanied by a variable inflammatory response within the synovial membrane. A principal defect in hyaline cartilage at the articular surface of a joint is the alteration in the ratio of glycosaminoglycans to the collagen fiber content of the matrix. Bones directly underlying cartilage in the joints are called subchondral bones. These subchondral bones nourish the overlying cartilage which itself is devoid of blood vessels, nerves or lymphatic tissue.

A natural erosion of cartilage occurs with age, but may also result from excessive loads placed on joints, obesity, heredity, trauma, decreased circulation, poor bone alignment and repetitive stress may exacerbate the condition of the joint. It is postulated that free radical damage may contribute to the development of osteoarthritis.

Cells of hyaline cartilage known as chondrocytes produce and maintain the surrounding extracellular matrix. Maintenance of homeostatis of the cartilage matrix depends upon catabolism of matrix proteins such as type II collagen and aggrecan. These proteins are digested and replaced by new proteins synthesized by chondrocytes. Catabolism is in part carried out by proteolytic enzymes such as matrix metalloproteinase (MMP) and aggrecanase proteins. In a normal animal, a balance is achieved between synthesis and degradation, thereby maintaining healthy cartilage. When the balance shifts to degradation, pathogenesis ensues and may result in joint inflammation and osteoarthritis.

A homeostatic condition in cartilage is dependent upon regulation through intercellular signaling between chondrocytes. Chondrocytes thus produce and respond to signaling molecules. Such signaling molecules may comprise cytokines and growth factors which may directly influence cellular metabolism. Intercellular signaling is complex and has not been fully characterized. Growth factor molecules such as TGF-beta are involved and believed to promote type II collagen production and to, inhibit collagen cleavage. Cytokines, such as TNF-alpha and IL-1-beta, also play a role. These cytokines are believed to promote production of proteases that may degrade cartilage. Numerous other complex interactions are believed to be occurring as a result of intercellular signaling.

Due to the complexity of the intercellular signaling process, it is highly desirable to understand at a genetic level the interactions that are taking place. Detection of dysregulated genes in a pre-arthritic or an arthritic condition is helpful in understanding the biology of abnormal musculoskeletal joint disorders, especially on a genome-wide basis. A more detailed understanding of the biological pathways involved through gene expression profiling will aid in the development of salutary pharmaceutical, nutraceutical and nutritional (dietary) interventions in the disease pathways. These approaches may enable prevention, early detection and treatment of the underlying abnormal musculoskeletal joint conditions as well as in monitoring the prognosis of such abnormal musculoskeletal joint disorders, especially in osteoarthritis. Dysregulated genes involved in the pathology of such disorders may serve as important biomarkers to optimize selection of appropriate pharmaceutical, nutraceutical and nutritional (dietary) interventions.

There is yet to be identified a drug that reverses the course of osteoarthritis. Currently available therapeutic agents are employed to reduce inflammation and/or to relieve pain. Current therapy employs a class of drugs known as non-steroidal anti-inflammatory drugs (NSAIDs) to treat musculoskeletal joint disorders such as osteoarthritis, but these therapies have a variety of drawbacks, including, in particular, gastrointestinal disorders and they may also inhibit cartilage formation.

Large dogs may develop arthritis as they age. Large dog breeds are more susceptible to arthritis due to their increased mass and/or genetic disposition. Large dogs are not the only animals at risk of arthritis and other cartilage conditions. Arthritis and other degenerative joint diseases have been commonly recognized in dogs and such conditions have been shown to be prevalent in cats. Feline osteoarthritis is a disease primarily affecting aged felines ten years of age or older. Animals at risk of developing cartilage-affecting abnormal musculoskeletal joint disorders include, but are not limited to, mammals such as canine, feline, equine, hircine, ovine, porcine, bovine, human and non-human primate species, and birds including turkeys and chickens.

Diet plays an important role in disease causation and progression because it is fundamentally involved in metabolism. Disease regulated genes are at some level regulated by nutritional factors. Thus, dietary components present in foods as nutrients may regulate gene expression at the transcriptional and translational level, as well as in certain post-translational modifications. They may similarly be involved in degradation and enzymatic activities. Nutrient levels may influence the equilibrium of metabolic pathways. Metabolic pathways are frequently complex and may involve many redundancies and interrelationships among different metabolic pathways. Altering the concentration of a single enzyme, growth factor, cytokine or metabolite may impact a number of metabolic pathways involved in disease-related physiology. Hormones and other cell signaling molecules are well-understood to be regulated by diet and are also known to be implicated in the development and progression of disease.

The same disease phenotype may result from disturbances in different metabolic pathways, and the genetic make-up of each animal differs, thereby causing variation in responses to the same factors, including nutritional and environmental factors. The interplay of genetic, nutritional and environmental factors is important in understanding the etiology, prevention, treatment and progression of diseases in animals. Finding gene expression responses to nutrients associated with various diseases and disorders permits formulation of diets for animals susceptible to disease such as abnormal musculoskeletal joint disorders, and further permits diagnosis, treatment and monitoring the prognosis of the underlying disease.

Nutritional components influence gene expression, including mRNA production (transcription), mRNA processing, protein production (translation) and post-translational modifications, thereby influencing the overall metabolic status of an animal. As a result, the use of biomarkers for early detection and monitoring of disease progression and/or genotype-based diets may enable prevention or treatment of diseases as well as new therapies to be developed for animals, particularly for companion animals. Diet is arguably the most important environmental factor affecting the phenotype of an animal, including susceptibility to disease.

Gene expression may be regulated through unstable processes that are controlled by activators and repressors of gene function. Nutritional status may cause significant changes in gene transcription rates. Macronutrients such as glucose, fatty acids and amino acids and micronutrients such as iron, zinc and vitamins can regulate gene expression. Various bioactive food components such as carotenoids, flavonoids, monoterpenes and phenolic acids may act as transcription factors affecting gene expression. These substances tend to have direct effects on gene expression. In other situations, substances like dietary fiber, which is fermented in the gut by bacteria, may lead to the production of nutrients such as short chain fatty acids. Such substances may act as indirect activators or repressors of gene expression.

Identification of nutrient-related changes upon transcription and translation may be detected in experiments of the type described in this specification. In view of the extensive array of genes profiled in the examples of this specification, alterations in gene expression and quantification are readily detected by the methods taught in this specification. Thus, dietary and metabolic gene expression signatures may be readily ascertained using the techniques taught in the Examples of this specification. Biomarkers of the invention are proteins and/or nucleic acids that are differentially expressed in animals. Biomarker expression can be assessed at the protein or nucleic acid level using various methods known to the skilled artisan.

Only very limited work has been done to date in screening the canine and feline genomes for gene expression profiles in response to nutritional components in the diet of these companion animals. Work has been done in the area of cancer employing a canine gene microarray for CG analysis of tumors. Thomas R. et al. A canine cancer gene microarray for CGH analysis tumors, Cyrogenet. Genome Res., 2003; 102:254-260. Further works has been done in the area of dilated cardiomyopathy. Oyayma, M. A. et al., Genomic expression patterns of cardiac tissue from dogs with dilated cardiomyopathy, Am. J. Vet. Res. 2005; 66:1140-1155. To date the study of the canine genome with respect to osteoarthritis has been very limited. In one study, the MIG-6 gene was found to be elevated in dogs in the high risk osteoarthritis group and it has been hypothesized that this gene may be implicated in cartilage degradation and in the production of cartilage in dogs. Mateescu, R. G. et al., Increased MIG-6 mRNA transcripts in osteoarthritic cartilage. Biochem. Biophy. Res. Commun. 2005; 332:482-486.

Studies in healthy populations of animals versus populations having a disease such as the abnormal musculoskeletal joint disorders described in this specification have not been extensively conducted. Little data is available with respect to the canine genome and far less with respect to the feline genome. Gene expression data contained in this specification identifies genes associated with cartilage degradation in dogs and cats. Such gene expression data enables identification of nutritional compositions capable of modulating expression of such genes in a favorable manner. This is also the case with respect to genes generally associated with inflammation. Analogous data in felines is additionally set forth in the specification, figures and examples of this specification.

Gene expression data contained in the specification and examples enables a variety of desirable inventions based on the gene expression profiles described herein. The data permits identification and quantification of gene expression products as biomarkers of nutrition as well as disease prevention, identification and treatment of the underlying abnormal musculoskeletal joint disorder. Gene expression data elicited as a result of the practice of the methods of the invention also permits monitoring the progression of such abnormal musculoskeletal joint disorders. These inventions further include genetic testing to identify susceptible subpopulations of animals likely to be afflicted with such abnormal musculoskeletal joint disorders, to identify optimal diets for the prevention or treatment of such disorders, to identify pharmaceutical, nutraceutical and nutritional (dietary) interventions based on the findings set forth in this specification in order to treat the underlying diseases and inflammation. The inventions also include biomarkers for early disease detection, targeted therapeutics, diagnostic reagents and kits for the analysis of tissue and blood samples from animals susceptible to or having such abnormal musculoskeletal joint disorders.

In designing foods for animals, for example, companion animals such as cats and dogs, optimal animal health or wellness through good nutrition is an important goal. However, even the most nutritious animal food is of little value if the animal rejects or refuses to eat the food, or if the animal's intake of the food is restricted because the animal finds the food unpalatable. Thus, the inventions set forth in this specification further comprise nutritional compositions capable of promoting the health and wellness of animals susceptible to or having such abnormal musculoskeletal joint disorders. The invention thus encompasses edible food compositions for companion animals, which have therapeutic and prophylactic efficacy and possess increased palatability over currently marketed companion animal food products.

SUMMARY OF THE INVENTION

The invention relates to compositions comprising at least one omega-3 fatty acid, at least one glycosaminoglycan, at least one amino sugar, at least one antioxidant, and carnitine or acetylcarnitine. The invention includes, but is not limited to, nutritional compositions, dietary supplements, nutraceuticals and treats for administration to animals, especially companion animals.

The invention also relates to methods of treating animals having an abnormal musculoskeletal joint condition, the methods comprising administering to the subject at least one of the compositions of the invention.

The invention still further relates to methods of delaying the onset in an animal or reducing the pain of an animal having an abnormal musculoskeletal joint condition, the methods comprising administering to the subject at least one of the compositions of the present invention.

In one embodiment, the invention encompasses a canine pet food composition comprising at least one omega-3 fatty acid, at least one glycosaminoglycan, at least one amino sugar, at least one antioxidant, and carnitine or acetylcarnitine.

In another embodiment, the invention encompasses a feline pet food composition comprising at least one omega-3 fatty acid, at least one glycosaminoglycan, at least one amino sugar, at least one antioxidant, and carnitine or acetylcarnitine.

Another embodiment encompasses a method of treating or preventing an abnormal musculoskeletal joint disorder in an animal in need thereof with a composition of the invention.

Yet another embodiment encompasses a method of treating or preventing an abnormal musculoskeletal joint disorder, selected from the group consisting of osteoarthritis, rheumatoid arthritis and local joint inflammation, in an animal in need thereof with a composition of the invention.

A still further embodiment of the invention encompasses a method of treating or preventing a musculoskeletal joint disorder selected from the group consisting of osteoarthritis, rheumatoid arthritis and local joint inflammation in a companion animal in need thereof with a composition of the invention.

Another embodiment of the invention encompasses a method of treating or preventing a musculoskeletal joint disorder, selected from the group consisting of osteoarthritis, rheumatoid arthritis and local joint inflammation, in a canine in need thereof with a composition of the invention.

Another embodiment of the invention encompasses a method of treating or preventing a musculoskeletal joint disorder, selected from the group consisting of osteoarthritis, rheumatoid arthritis and local joint inflammation, in a feline in need thereof with a composition of the invention.

Another embodiment of the invention encompasses a method of treating or preventing osteoarthritis in a canine in need thereof with a composition of the invention.

Another embodiment of the invention encompasses a method of treating or preventing osteoarthritis in a feline in need thereof with a composition of the invention.

Another embodiment of the invention encompasses a method of treating or preventing rheumatoid arthritis in a canine in need thereof with a composition of the invention.

Another embodiment of the invention encompasses a method of treating or preventing rheumatoid arthritis in a feline in need thereof with a composition of the invention.

Another embodiment of the invention encompasses a method of treating or preventing joint inflammation in a canine in need thereof with a composition of the invention.

Another embodiment of the invention encompasses a method of treating or preventing joint inflammation in a feline in need thereof with a composition of the invention.

Another embodiment of the invention encompasses one or more genes or gene segments that are differentially expressed in animals having an abnormal musculoskeletal joint disorder, which may include by way of example osteoarthritis, rheumatoid arthritis or local joint inflammation, compared with animals not having such an abnormal musculoskeletal joint disorder.

Another embodiment of the invention encompasses combinations of two or more polynucleotides or polypeptides that are differentially expressed in animals having an abnormal musculoskeletal joint disorder, which may include by way of example osteoarthritis, rheumatoid arthritis or local joint inflammation, compared with animals not having such an abnormal musculoskeletal joint disorder.

Another embodiment of the invention encompasses compositions of two or more polynucleotide or polypeptide probes suitable for detecting the expression of genes differentially expressed in animals having an abnormal musculoskeletal joint disorder, which may include by way of example osteoarthritis, rheumatoid arthritis or local joint inflammation, compared with animals not having such an abnormal musculoskeletal joint disorder.

Another embodiment of the invention encompasses methods and compositions for detecting the differential expression of one or more genes differentially expressed in animals having an abnormal musculoskeletal joint disorder, which may include by way of example osteoarthritis, rheumatoid arthritis or local joint inflammation, compared with animals not having such a musculoskeletal disorder.

Another embodiment of the invention encompasses methods for measuring the effect of a test substance on the expression profile of one or more genes differentially expressed in animals having an abnormal musculoskeletal joint disorder, which may include by way of example osteoarthritis, rheumatoid arthritis or local joint inflammation, compared with animals not having such an abnormal musculoskeletal disorder as a method for screening a test substance to determine if it is likely to be useful for modulating such disorder in such animal.

Another embodiment of the invention encompasses methods for formulating a prognosis that an animal is likely to develop an abnormal musculoskeletal joint disorder, which may include by way of example osteoarthritis, rheumatoid arthritis or local joint inflammation or in developing a diagnosis that an animal has such a musculoskeletal joint disorder.

A further aspect of the invention is that it relates to the identification of novel biomarkers of abnormal musculoskeletal joint disorders, particularly osteoarthritis, in animals, particularly companion animals, as well as methods of detection of abnormal musculoskeletal joint disorders in such animals based on a characteristic pattern of gene expression of such biomarkers in vivo. Specifically, the methods of the invention comprise detecting differential expression, compared to a control expression level, of at least one biomarker, in a body sample, preferably a blood sample, wherein the detection of differential expression of such biomarker specifically identifies animals that have an abnormal musculoskeletal joint disorder, especially osteoarthritis. Thus, such methods rely upon the detection of at least one biomarker that is differentially expressed in an abnormal musculoskeletal joint disorder in comparison to cells from normal or control animals.

It is also an embodiment of the invention to modulate various canine biomarkers related to an abnormal musculoskeletal joint disorder, in particular osteoarthritis, rheumatoid arthritis, or a local joint inflammatory condition by administering a composition of the invention to an animal in need thereof in an amount effective to modulate the biomarker. Examples of biomarkers related to an abnormal musculoskeletal joint disorder that can be modulated include, but are not limited to, Annexin A1, Cathepsin D, Cathepsin F, Cathepsin S, RELA, HMGB1, IL-1β, TNFα, TNFβ, TLR-2, TLR-4, p38 MAPK, TIMP-1, TIMP-2, MMP-1, MMP-2, MMP-13, IL-15 and IL-17 receptor, COL2A1, COL1A2, COL3A1, COL4A1, MMP-13, TIMP-2, MMP-2, C2C, C1,2C, FLAP, PLA2, MAPK1, MAPK2 and Aggrecan.

The biomarkers of the invention are proteins and/or nucleic acids that are differentially expressed in an animal having or likely to develop an abnormal musculoskeletal joint disorder, in particular osteoarthritis, rheumatoid arthritis or a local joint inflammatory condition.

It is further contemplated herein that the methods of the present invention may be used in combination with traditional diagnostic techniques that are able to detect the physical and morphological characteristics of degenerative musculoskeletal joint disease. Thus, for example, the characterization of differential expression in genes for osteoarthritis biomarkers in cells obtained from a blood sample of an animal may be combined with conventional diagnostic (e.g., radiological) techniques in order to corroborate a diagnosis of osteoarthritis.

In a further aspect, the invention relates to compositions comprising one or more nucleic acid probes that specifically hybridize to a nucleic acid, or fragment thereof, encoding a biomarker of the present invention.

In an additional aspect, the invention relates to compositions comprising antibodies that specifically bind to a polypeptide encoded by a gene expressing a biomarker of the present invention.

The invention also relates to kits to diagnose an abnormal musculoskeletal join disorder in an animal comprising component that can be used to detect expression of the biomarkers of the present invention, including, but not limited to, the compositions and microarrays described herein.

In another aspect, it is also contemplated herein that the invention relates to methods for identifying bioactive dietary components or other natural compounds (referred to hereafter as "dietary components" or "components") that may be tested for their ability to treat or ameliorate an abnormal musculoskeletal joint condition in an animal comprising: (a) contacting a cell capable of expressing an RNA or protein product of one or more biomarkers disclosed in Table 2 and/or Table 3 with a test component; (b) determining the amount of said RNA and/or product produced in the cells contacted with the test component; and (c) comparing the amount of said RNA and/or protein product in the cells contacted with the test component to the amount of the same said RNA or protein product present in a corresponding control cell that has not been contacted with the test component; wherein if the amount of the RNA or protein product is altered relative to the amount in the control, the component is identified as one to be tested for its ability to treat or ameliorate an abnormal musculoskeletal joint disorder, especially osteoarthritis, rheumatoid arthritis or a local joint inflammatory condition.

A further aspect of the invention is a method for diagnosis and/or prognosis of osteoarthritis in an animal, wherein the method comprises the steps of: obtaining at least one tissue sample or bodily fluid specimen from the animal; determining the amount of one or more biomarkers selected from Table 2 and/or Table 3 in said at least one sample or specimen obtained from the animal, wherein said biomarker is a polypeptide, protein, RNA, DNA, polynucleotide or metabolite thereof. A still further embodiment is such method where such one or more biomarkers is selected from the group consisting of Annexin A1, Cathepsin D, Cathepsin F, Cathepsin S, RELA, HMGB1, IL-1B, TNFα, TNFβ, TLR-2, TLR-4, p38 MAPK, TIMP-1, TIMP-2, MMP-1, MMP-2, MMP-13, IL-15 and IL-17 receptor.

Yet another embodiment of the invention is a kit for diagnosis and/or prognosis of osteoarthritis in an animal, particularly for carrying out the method for diagnosis and/or prognosis of osteoarthritis in an animal, wherein the method comprises the steps of: obtaining at least one tissue sample or bodily fluid specimen from the animal; determining the amount of one or more biomarkers selected from Table 2 and/or Table 3 in said at least one sample or specimen obtained from the animal, wherein said biomarker is a polypeptide, protein, RNA, DNA, polynucleotide or metabolite thereof, and optionally, further comprising a detectable agent linked to said biomarker.

A still further embodiment of the invention is a reagent for diagnosis and/or prognosis of osteoarthritis in an animal, particularly for carrying out the method for diagnosis and/or prognosis of osteoarthritis in an animal, wherein the method comprises the steps of: obtaining at least one tissue sample or bodily fluid specimen from the animal; determining the amount of one or more biomarkers selected from Table 2 and/or Table 3 in said at least one sample or specimen obtained from the animal, wherein said biomarker is a polypeptide, protein, RNA, DNA, polynucleotide or metabolite thereof, and optionally further comprising a detectable agent linked to said biomarker.

Another embodiment of the invention is the use of one or more polypeptides, proteins, RNAs, DNAs, polynucleotide or metabolites thereof, as identified on Table 2 and/or Table 3, as a biomarker for diagnosis and/or prognosis of an abnormal musculoskeletal joint disorder, particularly for forming a kit for diagnosis or prognosis of an abnormal musculoskeletal joint disorder. A still further embodiment is such kit where such one or more biomarkers is selected from the group consisting of Annexin A1, Cathepsin D, Cathepsin F, Cathepsin S, RELA, HMGB1, IL-1β, TNFα, TNFβ, TLR-2, TLR-4, p38 MAPK, TIMP-1, TIMP-2, MMP-1, MMP-2, MMP-13, IL-15 and IL-17 receptor. Yet another embodiment is such kit, wherein the reagents and equipment comprise DNA microarray analysis materials including oligonucleotide microarray, c-DNA microarray, and focused gene chip, or a combination thereof.

Another embodiment of the invention is a method of detecting osteoarthritis in an animal, comprising providing a sample from the animal comprising a tissue sample or specimen of a bodily fluid; detecting levels of a biomarker, as identified on Table 2 and/or Table 3, which is a polypeptide, protein, RNA, DNA, polynucleotide or metabolite thereof in the sample or specimen; and comparing the levels of said biomarker in the sample or specimen to levels of said biomarker in a control sample; wherein expression of the biomarker has at least a 1-fold or greater difference in gene expression compared with expression in a cell of a control animal.

A still further embodiment of the invention is a method of detecting osteoarthritis in an animal, comprising contacting the sample or specimen of the aforesaid method with a first primer that comprises a polynucleotide sequence that hybridizes selectively to said biomarker and a second primer comprising a polynucleotide sequence that hybridizes to said biomarker polynucleotide, performing an amplification reaction, and quantifying an amplification product of the biomarker polynucleotide in the sample or the specimen.

Another embodiment of the invention is a method of assessing the effectiveness of a course of treatment or nutritional management for an animal suffering from osteoarthritis, the method comprising (a) measuring a first level of a biomarker polypeptide, protein, RNA, DNA, polynucleotide or metabolite thereof, as identified on Table 2 and/or Table 3, in a tissue sample or a specimen of bodily fluid from said animal at a first time point in time during the course of treatment, (b) measuring a second level of said biomarker in said sample or specimen from said animal at a second point in time during the course of treatment, and (c) comparing the measurements of the biomarker at said first point and said second point; wherein expression of the biomarker has at least an 1-fold or greater difference in gene expression compared with expression in a cell of a control animal.

Another embodiment of the invention is a method of assessing the progression of a course of treatment or nutritional management for an animal suffering from osteoarthritis, the method comprising (a) measuring a first level of a biomarker polypeptide, protein, RNA, DNA, polynucleotide or metabolite thereof, as identified on Table 2 and/or Table 3, in a tissue sample or a specimen of bodily fluid from said animal at a first point in time during the course of treatment, (b) measuring a second level of said biomarker in said sample or specimen from said animal at a second point in time during the course of treatment, and (c) comparing the measurements of the biomarker at said first point and said second point; wherein expression of the biomarker has at least an 1-fold or greater difference in gene expression compared with expression in a cell of a control animal.

A further embodiment of the invention is a method for identifying a molecule for diagnosing osteoarthritis in an animal, the method comprising: (1) providing a sample of a tissue sample or a specimen of bodily fluid from said animal comprising a biomarker, as identified on Table 2 and/or Table 3, which is a polypeptide, protein, RNA, DNA, polynucleotide or metabolite thereof; (2) contacting the sample or specimen with a test molecule; (3) determining whether the test molecule binds to, or is bound by, said biomarker; wherein expression of the biomarker has at least an 1-fold or greater difference in expression compared with expression of said biomarker of a control animal.

A still further embodiment of the invention is a method for screening for osteoarthritis in an animal comprising the steps of: i) obtaining a tissue sample or a specimen of bodily fluid from said animal and determining a gene expression profile of one or more biomarker polypeptides, proteins, RNAs, DNAs, polynucleotides or metabolites in the sample; and ii) comparing the gene expression profile of said one or more biomarkers in the sample to a positive control comprising an average gene expression level of said one or more biomarkers in a plurality of reference samples that are derived from animals displaying symptoms of osteoarthritis to determine differential gene expression between the sample and the positive control, wherein presence of osteoarthritis is indicated if there is no statistically significant differential gene expression between the gene expression profile of one or more biomarkers in the sample and the positive control, wherein the biomarkers comprise one or more genes of Table 2 and/or Table 3.

Yet another embodiment of the invention is a method for screening for osteoarthritis in an animal comprising the steps of: i) obtaining a tissue sample a specimen of bodily fluid from said animal and determining a gene expression profile of one or more biomarker polypeptides, proteins, RNAs, DNAs, polynucleotides or metabolites in the sample; and ii) comparing the gene expression profile of said one or more biomarkers in the sample to a positive control comprising an average gene expression level of said one or more biomarkers in a plurality of reference samples that are derived from control animals displaying no symptoms of osteoarthritis to determine differential gene expression between the sample and a reference sample of said control animals, wherein presence of osteoarthritis is indicated if there is a 1-fold differential gene expression between the gene expression profile of one or more biomarkers in the sample and the positive control, wherein the biomarkers comprise one or more genes of Table 2 and/or Table 3.

Another embodiment of the invention is an assay for screening an agent for its ability to treat or prevent one or more symptoms of osteoarthritis comprising the steps of: i) isolating a nucleic acid control sample from a tissue sample from said animal that produces a differential gene expression profile representative of osteoarthritis and determining the level of gene expression in the control sample; ii) subjecting the tissue sample to said agent; iii) isolating a nucleic acid test sample from said tissue sample after subjecting said tissue sample to the agent of step (ii) and determining the level of gene expression in the test sample; iv) comparing production, stability, degradation and/or activation of gene expression between the control sample and the test sample to find the differential gene expression profile between the test sample and the control sample; wherein a differential gene expression profile between the test sample as compared with the control sample is indicative of the ability of the agent to prevent or treat one or more symptoms of osteoarthritis.

Still another embodiment of the invention is a method for identifying a plurality of genes that are differentially expressed between tissue samples for use in an informative array, comprising: providing a first set of heterogeneous nucleic acid probes derived from a first tissue sample; providing a second set of heterogeneous nucleic acid probes derived from a second tissue sample; hybridizing a nucleic acid array comprising a plurality of sequences derived from genes of a biological process with the first set of probes and determining a first level of expression for sequences of the array; hybridizing the array with said second set of probes and determining a second level of expression for sequences of the array; identifying a plurality of genes that are differentially expressed in said biological process by comparing the first level of expression with said second level of expression for hybridized sequences; and establishing a ranking of the identified genes by a step selected from the group of steps consisting of: determining an absolute value of the difference between the first level of expression and the second level of expression, and ranking genes having a higher difference over genes having a lower difference; and determining a standard deviation of the difference between the first level of expression and the second level of expression, and ranking genes having a higher standard deviation over genes having a lower standard deviation, wherein the genes comprise one or more genes on Table 2 and/or Table 3.

Another embodiment of the invention is a method for converting a nucleic acid array into an informative array comprising: providing a first set of heterogeneous nucleic acid probes derived from a first tissue sample; providing a different, second set of heterogeneous nucleic acid probes derived from a second tissue sample; hybridizing a nucleic acid array comprising a plurality of sequences with the first set of probes and determining a first level of expression for sequences of the array; hybridizing the array with said second set of probes and determining a second level of expression for sequences of the array; identifying a plurality of genes that are differentially expressed in said biological process based on a difference between the first level of expression and the second level of expression for identified genes, by a step selected from the group of steps consisting of: determining an absolute value for the difference between the first level of expression and the second level of expression, and ranking genes having a higher difference over genes having a lower difference; and determining a standard deviation of the difference between the first level of expression and the second level of expression, and ranking genes having a higher standard deviation over genes having a lower standard deviation; and selecting genes from the plurality of identified differentially expressed genes for inclusion on the informative array, wherein said genes are selected from the genes listed in Table 2 and/or Table 3.

Yet another embodiment of the invention is a computer-implemented method for analyzing gene expression to screen for osteoarthritis comprising the steps of: i) compiling data comprising a plurality of measured gene expression signals derived from nucleic acid microarray analysis, selected from the group consisting of oligonucleotide microarray, c-DNA microarray, and focused gene chip analysis, or a combination thereof, of tissue samples into a form suitable for computer-based analysis: and ii) analyzing the compiled data, wherein the analyzing comprises identifying gene networks from a number of upregulated biomarker genes and down-regulated biomarker genes, wherein the biomarker genes are genes that have been identified as associating with presence or severity of osteoarthritis, said genes comprising genes listed in Table 2 and/or Table 3.

Another embodiment of the invention is a method of in vitro screening a drug candidate, the method comprising determining the capacity of the candidate to modulate expression of a selected gene or activity of the selected gene expression product wherein the selected gene or gene expression product is an osteoarthritis biomarker or gene expression product selected from the group consisting of the genes or gene products listed on Table 2 and/or Table 3.

Another embodiment of the invention is a method of in vitro screening a nutritional foodstuff, dietary supplement, nutraceutical or treat, the method comprising determining the capacity of the candidate to modulate expression of a selected gene or activity of the selected gene expression product wherein the selected gene or gene expression product is an osteoarthritis biomarker or gene expression product selected from the group consisting of the genes or gene products listed on Table 2 and/or Table 3.

Another embodiment of the invention is a method of in vitro screening a drug candidate, the method comprising a) collecting at least two biological samples; wherein a first sample mimics osteoarthritis and a second sample mimics a healthy condition; b) contacting at least one sample or a mixture of samples with one or more drug candidates to be tested; c) measuring gene expression or gene expression product level or activity of genes listed on Table 2 and/or Table 3 or activity in the biological samples or mixture obtained in b); and d) selecting drug candidates which are capable of modulating gene expression or gene expression product level or activity measured in the samples or mixture obtained in b) and comparing the levels with a sample not mixed with the drug candidate.

Another embodiment of the invention is a method of in vitro screening a nutritional foodstuff, dietary supplement, nutraceutical or treat, the method comprising a) collecting at least two biological samples; wherein a first sample mimics osteoarthritis and a second sample mimics a healthy condition; b) contacting at least one sample or a mixture of samples with one or more nutritional foodstuff, dietary supplement, nutraceutical or treat to be tested; c) measuring gene expression or gene expression product level or activity of genes listed on Table 2 and/or Table 3 or activity in the biological samples or mixture obtained in b); and d) selecting a nutritional foodstuff, dietary supplement, nutraceutical or treat which is capable of modulating gene expression or gene expression product level or activity measured in the samples or mixture obtained in b) and comparing the levels with a sample not mixed with the nutritional foodstuff, dietary supplement, nutraceutical or treat.

Another embodiment of the invention is a method of in vitro determination of an animal's sensitivity to osteoarthritis, the method comprising comparing gene expression or gene expression product levels or activity of biomarkers selected from the group consisting of the genes and gene products listed on Table 2 and/or Table 3.

Another embodiment of the invention is a method of preparing a composition for treating osteoarthritis, the method comprising preparing a composition comprising a modulator of osteoarthritis biomarkers selected from the group consisting of genes and gene products listed on Table 2 and/or Table 3.

Another embodiment of the invention is a method of determining the efficacy of a treatment for osteoarthritis, comprising the steps of: (a) providing a biological sample from an animal affected by osteoarthritis, who has been subjected to said treatment, (b) determining the level in said sample of one or more biomarkers for osteoarthritis, to create an expression profile for said animal, and (c) comparing said expression profile with: i) a comparable expression profile obtained from said test animal before initiation of said treatment, and/or ii) a comparable expression profile obtained from said test animal at an earlier stage of said treatment, and/or iii) a comparable expression profile characteristic of a subject who is unaffected by osteoarthritis, wherein the one or more biomarkers for osteoarthritis, comprise expression products of one or more genes shown in Table 2 and/or Table 3.

Another embodiment of the invention is a method of selecting a food composition for an animal for its ability to treat or prevent one or more symptoms of osteoarthritis, comprising the steps of: i) accessing at least one database that comprises a first data set relating a gene expression profile of a tissue sample or a biological fluid specimen of a tissue sample from an animal having osteoarthritis; ii) accessing a least one database that comprises a second data set relating to effects of bioactive dietary components on said gene expression profile; and iii) by use of a first algorithm using said first and said second data sets, processing said first data set and said second data set to derive a nutritional formula useful for selecting and preparing a food composition for said animal; and iv) storing or using said nutritional formula in a user readable format.

Other and further objects, features, and advantages of the present invention will be readily apparent to those skilled in the art.

BRIEF DESCRIPTION OF THE DRAWINGS

FIG. 4 depicts one embodiment of the compositions of the present invention identified as composition j/d.

DETAILED DESCRIPTION OF THE INVENTION

Figure 1:
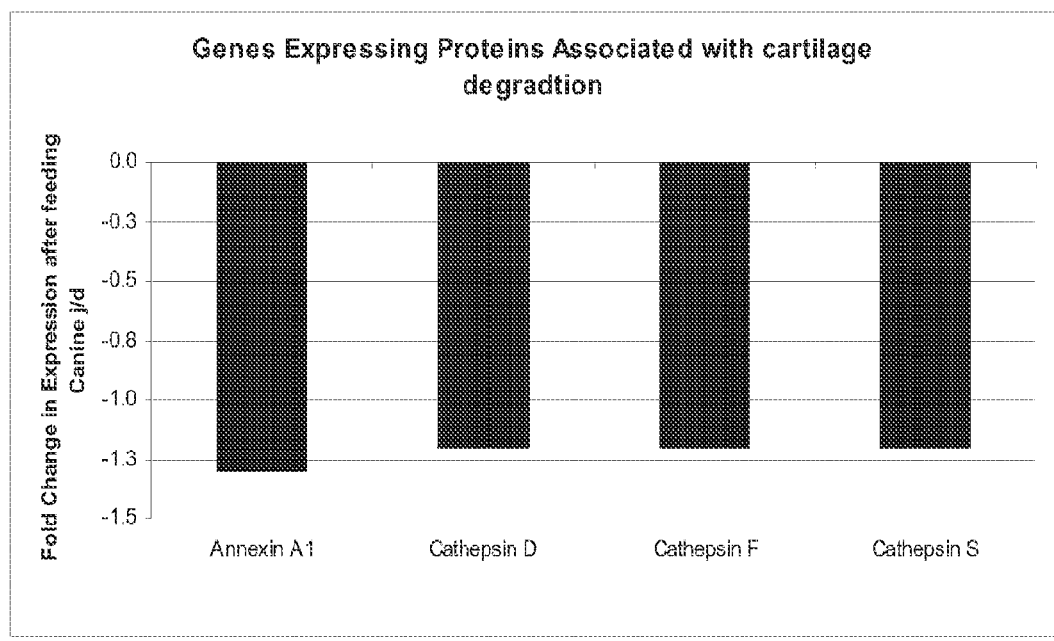
FIG. 1 depicts a decrease in gene expression of various genes associated with cartilage degradation in dogs after being fed at least one composition of the invention identified as canine composition j/d.
Figure 2:
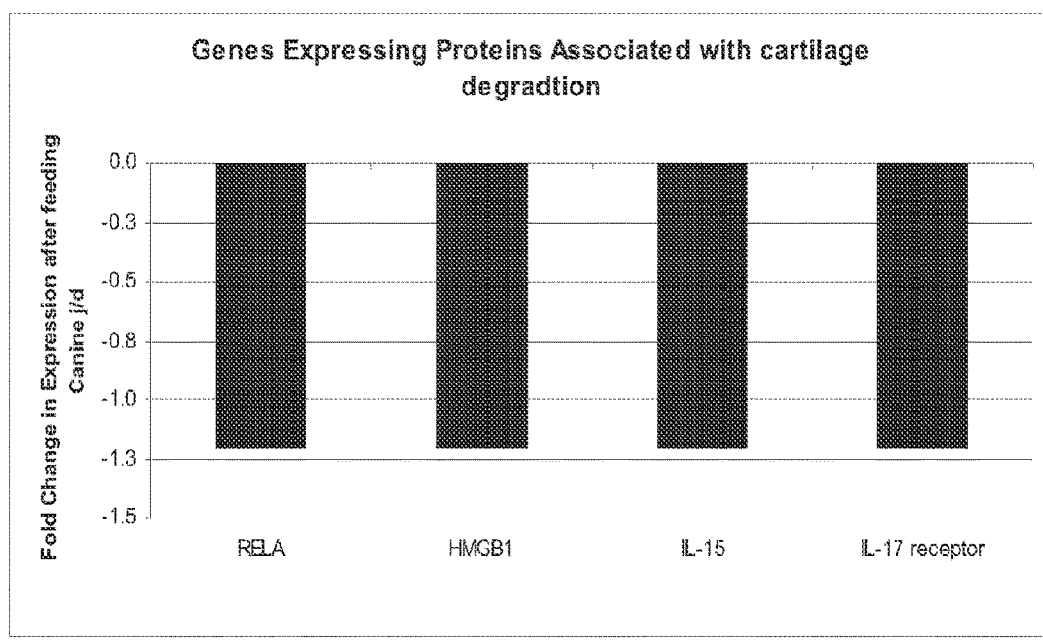
FIG. 2 depicts a decrease in gene expression of various genes associated with cartilage degradation in dogs after being fed at least one composition of the invention identified as canine composition j/d.

The invention relates to compositions and methods of treating abnormal conditions in an animal, wherein the abnormal condition affects the musculoskeletal joints of the animal. The compositions can be formulated for oral administration, including but not limited to animal feeds. The animal feeds can be given to any type of animal for which the compositions have been formulated. For example, the feeds can be formulated for companion animals, including but not limited to, dogs or cats.

As used herein an abnormal animal is an animal that has been diagnosed with or is apparently suffering from a condition that affects the musculoskeletal joints in the animal or for which the gene expression data contained herein suggests a predisposition for such condition. For example, a dog or cat diagnosed with or apparently suffering from osteoarthritis would be considered an abnormal animal.

The compositions of the present invention comprise at least one omega-3 fatty acid. Omega-3 fatty acids are well known in the art. Omega-3 fatty acids are essential nutrients for the health of animals and such fatty acids either cannot be made or cannot be made in sufficient quantities by animals. Such fatty acids are employed as a dietary component or components in the compositions and methods taught by the inventions herein. The formulation of the nutritional compositions contained herein is based in part upon the impact of such nutritional compositions on gene expression in animals suffering from musculoskeletal joint disorders of the types described herein. Examples of omega-3 fatty acids include, but are not limited to, alpha-linoleic acid (ALA), docosahexanoic acid (DHA) and eicosapentaenoic acid (EPA). In one embodiment of the present invention, the composition comprises one of ALA, DHA or EPA. In another embodiment, the composition comprises at least two of ALA, DHA or EPA. In yet another embodiment of the present invention, the composition comprises all three of ALA, DHA and EPA.

The compositions also comprise at least one glycosaminoglycan (GAG). GAGs are well know in the art and are considered to be unbranched polysaccharides comprised of repeating disaccharide units. Provided that the polysaccharide is unbranched and comprised of repeating disaccharide units, the molecule or polymer is considered to be a GAG. Examples of GAGs include, but are not limited to, chondroitin sulfate, dermatan sulfate, keratan sulfate, heparin, heparan sulfate and hyaluronan. In one embodiment of the present invention, the composition comprises at least one of chondroitin sulfate, dermatan sulfate, keratan sulfate, heparin, heparan sulfate or hyaluronan. In another embodiment of the present invention, the composition comprises at least two of chondroitin sulfate, dermatan sulfate, keratan sulfate, heparin, heparan sulfate or hyaluronan. In yet another embodiment of the present invention, the composition comprises at least three of chondroitin sulfate, dermatan sulfate, keratan sulfate, heparin, heparan sulfate or hyaluronan. In still another embodiment of the present invention, the composition comprises at least four, five or all of chondroitin sulfate, dermatan sulfate, keratan sulfate, heparin, heparan sulfate and/or hyaluronan.

The compositions also comprise at least one amino sugar. An amino sugar is well understood in the art and simply means a sugar moiety wherein an amine group replaces or occurs in addition to a hydroxyl group. Examples of amino sugars include, but are not limited to, galactosamine, glucosamine, sialic acid and N-acetylglucosamine. In one embodiment of the present invention, the compositions comprise at least one of galactosamine, glucosamine, sialic acid or N-acetylglucosamine. In another embodiment of the present invention, the compositions comprise at least two of galactosamine, glucosamine, sialic acid or N-acetylglucosamine. In yet another embodiment of the present invention, the compositions comprise at least three of galactosamine, glucosamine, sialic acid or N-acetylglucosamine. In still another embodiment of the present invention, the compositions comprise all four of galactosamine, glucosamine, sialic acid or N-acetylglucosamine.

The compositions also comprise at least one antioxidant. Antioxidants are well known in the art. Examples of antioxidants include but are not limited to vitamin C, vitamin E (tocopherols and/or tocotrienols), glutathione, lipoic acid, melatonin, carnitine and beta-carotene. In one embodiment of the present invention, the compositions comprise at least one of vitamin C, vitamin E (tocopherols and/or tocotrienols), glutathione, lipoic acid, melatonin, or beta-carotene. In another embodiment of the present invention, the compositions comprise at least two of vitamin C, vitamin E (tocopherols and/or tocotrienols), glutathione, lipoic acid, melatonin, or beta-carotene. In yet another embodiment of the present invention, the compositions comprise at least three of vitamin C, vitamin E (tocopherols and/or tocotrienols), glutathione, lipoic acid, melatonin, or beta-carotene. In still another embodiment of the present invention, the compositions comprise at least four of vitamin C, vitamin E (tocopherols and/or tocotrienols), glutathione, lipoic acid, melatonin, or beta-carotene. In still another embodiment of the present invention, the compositions comprise at least five or more of vitamin C, vitamin E (tocopherols and/or tocotrienols), glutathione, lipoic acid, melatonin, and/or beta-carotene.

The compositions of the present invention also comprise carnitine or acetylcarnitine, which are quaternary ammonium compounds with antioxidant effects.

In select embodiments, the compositions further comprise at least one dietary mineral and/or at least one natural amino acid. Examples of dietary minerals and natural amino acids are well known. Examples of dietary minerals include, but are not limited to, calcium, chloride, magnesium, phosphorus, potassium, sodium, cobalt, copper, fluorine, iodine, iron, manganese, molybdenum, nickel, selenium, sulfur, zinc and vanadium. In one embodiment, the composition comprises at least one of calcium, chloride, magnesium, phosphorus, potassium, sodium, cobalt, copper, fluorine, iodine, iron, manganese, molybdenum, nickel, selenium, sulfur, zinc or vanadium. In another embodiment, the composition comprises at least two of calcium, chloride, magnesium, phosphorus, potassium, sodium, cobalt, copper, fluorine, iodine, iron, manganese, molybdenum, nickel, selenium, sulfur, zinc or vanadium. In yet another embodiment, the composition comprises at least three of calcium, chloride, magnesium, phosphorus, potassium, sodium, cobalt, copper, fluorine, iodine, iron, manganese, molybdenum, nickel, selenium, sulfur, zinc or vanadium. In still another embodiment, the composition comprises at least four of calcium, chloride, magnesium, phosphorus, potassium, sodium, cobalt, copper, fluorine, iodine, iron, manganese, molybdenum, nickel, selenium, sulfur, zinc or vanadium. In still another embodiment, the composition comprises at least five or more of calcium, chloride, magnesium, phosphorus, potassium, sodium, cobalt, copper, fluorine, iodine, iron, manganese, molybdenum, nickel, selenium, sulfur, zinc or vanadium.

The natural amino acids are well known in the art and are the amino acids found in proteins. In one specific embodiment, the composition comprises an essential amino acid, wherein the term essential amino acid is relative to the species of the subject. For example, essential amino acids for dogs and cats include Arginine, Methionine, Histidine, Phenylalanine, Isoleucine, Threonine, Leucine, Tryptophan, Lysine and Valine. Taurine may also be considered to be an essential amino acid in cats.

In one embodiment canine food composition j/d comprises a composition as generally set forth in FIG. 4, and includes a glycosaminoglycan in the form of chondroitin sulfate, and an amino sugar in the form of glucosamine hydrochloride as well as carnitine and at least one antioxidant. The composition may also contain additional sources of nutrients, for example: Ground Whole Grain Corn, Chicken By-Product Meal, Flaxseed, Soybean Mill Run, Brewers Rice, Soybean Meal, Pork Fat (preserved with mixed tocopherols and citric acid), Chicken Liver Flavor, Powdered Cellulose, Fish Oil, Potassium Chloride, L-Lysine, Calcium Carbonate, Choline Chloride, Iodized Salt, DL-Methionine, Vitamin E Supplement, vitamins (L-Ascorbyl-2-Polyphosphate (source of vitamin C), Vitamin E Supplement, Niacin, Thiamine Mononitrate, Vitamin A Supplement, Calcium Pantothenate, Biotin, Vitamin B12 Supplement, Pyridoxine Hydrochloride, Riboflavin, Folic Acid, Vitamin D3 Supplement), L-Threonine, Taurine, Soy Lecithin, Glucosamine Hydrochloride, minerals (Ferrous Sulfate, Zinc Oxide, Copper Sulfate, Manganous Oxide, Calcium Iodate, Sodium Selenite), L-Tryptophan, L-Carnitine, preserved with Mixed Tocopherols and Citric Acid, Chondroitin Sulfate, Beta-Carotene, Rosemary Extract.

The feline j/k food composition of the invention utilized in the Examples contained omega-3 fatty acids, omega-6 fatty acids and also contained alpha-linolenic acid. The composition contained a glycosaminoglycan in the form of chondroitin sulfate, and an amino sugar in the form of glucosamine hydrochloride. In addition, the composition contained carnitine and at least one antioxidant, for example, vitamin C and beta-carotene.

The term "animal" means a human or non-human animal, including avian, bovine, canine, equine, feline, hicrine, murine, ovine, primate, and porcine animals.

The term "antibody" means any immunoglobulin that binds to a specific antigen, including IgG, IgM, IgA, IgD, and IgE antibodies. The term includes polyclonal, monoclonal, monovalent, humanized, heteroconjugate, antibody compositions with polyepitopic specificity, chimeric, bispecific antibodies, diabodies, single-chain antibodies, and antibody fragments such as Fab, Fab', F(ab')$_2$, and Fv, or other antigen-binding fragments.

The term "array" means an ordered arrangement of at least two probes on a substrate. At least one of the probes is a control or standard and at least one of the probes is a diagnostic probe. The arrangement of from about two to about 40,000 probes on a substrate assures that the size and signal intensity of each labeled complex formed between a probe and a sample polynucleotide or polypeptide is individually distinguishable.

The term "differential expression" or "differentially expressed" means increased or unregulated gene expression or means decreased or downregulated gene expression as detected by the absence, presence, or at least two-fold, or at least a 1.5, 1.4, 1.3, 1.2, 1.1 or 1- fold change in the amount of transcribed messenger RNA or translated protein in a sample.

The term "fold" when used as a measure of differential gene expression means an amount of gene expression in an animal that is a multiple or a fraction of gene expression compared to the amount of gene expression in a comparison animal, e.g., an arthritic animal compared to a non-arthritic animal. For example, a gene that is expressed three times as much in the animal as in the comparison animal has a 3-fold differential gene expression and a gene that is expressed one-third as much in the animal as in the comparison animal also has a 3 fold differential gene expression.

The term "fragment" means (1) an oligonucleotide or polynucleotide sequence that is a portion of a complete sequence and that has the same or similar activity for a particular use as the complete polynucleotide sequence or (2) a peptide or polypeptide sequence that is a portion of a complete sequence and that has the same or similar activity for a particular use as the complete polypeptide sequence. Such fragments can comprise any number of nucleotides or amino acids deemed suitable for a particular use. Generally, oligonucleotide or polynucleotide fragments contain at least about 10, 50, 100, or 1000 nucleotides and polypeptide fragments contain at least about 4, 10, 20, or 50 consecutive amino acids from the complete sequence. The term encompasses polynucleotides and polypeptides variants of the fragments.

The term "gene" or "genes" means a complete or partial segment of DNA involved in producing a polypeptide, including regions preceding and following the coding region (leader and trailer) and intervening sequences (introns) between individual coding segments (exons). The term encompasses any DNA sequence that hybridizes to the complement of gene coding sequences.

The term "homolog" means (1) a polynucleotide, including polynucleotides from the same or different animal species, having greater than 30%, 50%, 70%, or 90% sequence similarity to a polynucleotide and having the same or substantially the same properties and performing the same or substantially the same function as the complete polynucleotide, or having the capability of specifically hybridizing to a polynucleotide under stringent conditions or (2) a polypeptide, including polypeptides from the same or different animal species, having greater than 30%, 50%, 70%, or 90% sequence similarity to a polypeptide identified by the expression of polynucleotides and having the same or substantially the same properties and performing the same or substantially the same function as the complete polypeptide, or having the capability of specifically binding to a polypeptide identified by the expression of polynucleotides. Sequence similarity of two polypeptide sequences or of two polynucleotide sequences is determined using methods known to skilled artisans, e.g., the algorithm of Karlin and Altschul (Proc. Natl. Acad. Sci. USA 87:2264-2268 (1990)). Such an algorithm is incorporated into the NBLAST and XBLAST programs of Altschul et al. (J. Mol. Biol. 215:403-410 (1990)). To obtain gapped alignments for comparison purposes, Gapped Blast can be utilized as described in Altschul et al. (Nucl. Acids Res. 25: 3389-3402 (1997)). When utilizing BLAST and Gapped BLAST programs, the default parameters of the respective programs (e.g., XBLAST and NBLAST) are used. See http://ww.ncbi.nlm.nih.gov.

The term "hybridization complex" means a complex that is formed between sample polynucleotides when the purines of one polynucleotide hydrogen bond with the pyrimidines of the complementary polynucleotide, e.g., 5'-A-G-T-C-3' base pairs with 3'-T-C-A-G-5'. The degree of complementarily and the use of nucleotide analogs affect the efficiency and stringency of hybridization reactions.

The term "in conjunction" means that a drug, food, or other substance is administered to an animal (1) together in a composition, particularly food composition, or (2) separately at the same or different frequency using the same or different administration routes at about the same time or periodically. "Periodically" means that the substance is administered on a dosage schedule acceptable for a specific substance. "About the same time" generally means that the substance (food or drug) is administered at the same time or within about 72 hours of each other. "In conjunction" specifically includes administration schemes wherein substances such as drugs are administered for a prescribed period and compositions of the present invention are administered indefinitely.

The term "polynucleotide" or "oligonucleotide" means a polymer of nucleotides. The term encompasses DNA and RNA (including cDNA and mRNA) molecules, either single or double stranded and, if single stranded, its complementary sequence in either linear or circular form. The term also encompasses fragments, variants, homologs, and alleles, as appropriate for the sequences that have the same or substantially the same properties and perform the same or substantially the same function as the original sequence. The sequences may be fully complementary (no mismatches) when aligned or may have up to about a 30% sequence mismatch. Preferably, for polynucleotides, the chain contains from about 50 to 10,000 nucleotides, more preferably from about 150 to 3,500 nucleotides. Preferably, for oligonucleotides, the chain contains from about 2 to 100 nucleotides, more preferably from about 6 to 30 nucleotides. The exact size of a polynucleotide or oligonucleotide will depend on various factors and on the particular application and use of the polynucleotide or oligonucleotide. The term includes nucleotide polymers that are synthesized and that are isolated and purified from natural sources. The term "polynucleotide" is inclusive of "oligonucleotide."

The term "polypeptide," "peptide," or "protein" means a polymer of amino acids. The term encompasses naturally occurring and non-naturally occurring (synthetic) polymers and polymers in which artificial chemical mimetics are substituted for one or more amino acids. The term also encompasses fragments, variants, and homologs that have the same or substantially the same properties and perform the same or substantially the same function as the original sequence. The term encompass polymers of any length, preferably polymers containing from about 2 to 1000 amino acids, more preferably from about 5 to 500 amino acids. The term includes amino acid polymers that are synthesized and that are isolated and purified from natural sources.

The term "probe" means (1) an oligonucleotide or polynucleotide, either RNA or DNA, whether occurring naturally as in a purified restriction enzyme digest or produced synthetically, that is capable of annealing with or specifically hybridizing to a polynucleotide with sequences complementary to the probe or (2) a peptide or polypeptide capable of specifically binding a particular protein or protein fragment to the substantial exclusion of other proteins or protein fragments. An oligonucleotide or polynucleotide probe may be either single or double stranded. The exact length of the probe will depend upon many factors, including temperature, source, and use. For example, for diagnostic applications, depending on the complexity of the target sequence, an oligonucleotide probe typically contains about 10 to 100, 15 to 50, or 15 to 25 nucleotides. In certain diagnostic applications, a polynucleotide probe contains about 100-1000, 300-600, nucleotides, preferably about 300 nucleotides. The probes herein are selected to be "substantially" complementary to different strands of a particular target sequence. This means that the probes must be sufficiently complementary to specifically hybridize or anneal with their respective target sequences under a set of predetermined conditions. Therefore, the probe sequence need not reflect the exact complementary sequence of the target. For example, a noncomplementary nucleotide fragment may be attached to the 5' or 3' end of the probe, with the remainder of the probe sequence being complementary to the target sequence. Alternatively, noncomplementary bases or longer sequences can be interspersed into the probe provided that the probe sequence has sufficient complementarity with the sequence of the target polynucleotide to specifically anneal to the target polynucleotide. A peptide or polypeptide probe may be any molecule to which the protein or peptide specifically binds, including DNA (for DNA binding proteins), antibodies, cell membrane receptors, peptides, cofactors, lectins, sugars, polysaccharides, cells, cell membranes, organelles and organellar membranes.

The term "sample" means any animal tissue or fluid containing, e.g., polynucleotides, polypeptides, antibodies, metabolites, and the like, including cells and other tissue containing DNA and RNA. Examples include, blood, cartilage, connective, epithelial, lymphoid, muscle, nervous, sputum, and the like. A sample may be solid or liquid and may be DNA, RNA, cDNA, bodily fluids such as blood or urine, cells, cell preparations or soluble fractions or media aliquots thereof, chromosomes, organelles, and the like.

The term "single package" means that the components of a kit are physically associated in or with one or more containers and considered a unit for manufacture, distribution, sale, or use. Containers include, but are not limited to, bags, boxes, bottles, shrink wrap packages, stapled or otherwise affixed components, or combinations thereof. A single package may be containers of individual food compositions physically associated such that they are considered a unit for manufacture, distribution, sale, or use.

The term "useful variations" means (1) for a polynucleotide, the complements of the polynucleotide; the homologs of the polynucleotide and its complements; the variants of the polynucleotide, its complements, and its homologs; and the fragments of the polynucleotide, its complements, its homologs, and its variants and (2) for a polypeptide, the homologs of the polypeptide; the variants of the polypeptide and its homologs; and the fragments of the polynucleotide, its homologs, and its variants.

The term "virtual package" means that the components of a kit are associated by directions on one or more physical or virtual kit components instructing the user how to obtain the other components, e.g., in a bag containing one component and directions instructing the user to go to a website, contact a recorded message, view a visual message, or contact a caregiver or instructor to obtain instructions on how to use the kit.

The term "standard" means (1) a control sample that contains tissue from a normal animal if, for example, an arthritic animal is being tested or tissue from, for example, an arthritic animal if a normal animal is being tested or (2) a control sample that contains tissue from a normal or, for example, arthritic animal that has not been exposed to a test substance being examined in the corresponding normal or, for example arthritic animal to determine if the test substance causes differential gene expression, as appropriate for the context of its use.

The term "stringent conditions" means (1) hybridization in 50% (vol/vol) formamide with 0.1% bovine serum albumin, 0.1% Ficoll, 0.1% polyvinylpyrrolidone, 50 mM sodium phosphate buffer at pH 6.5 with 750 mM NaCl, 75 mM sodium citrate at 42° C., (2) hybridization in 50% formamide, 5×SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 µg/ml), 0.1% SDS, and 10% dextran sulfate at 42° C.; with washes at 42° C. in 0.2×SSC and 0.1% SDS or washes with 0.015 M NaCl, 0.0015 M sodium citrate, 0.1% $Na_2SO_4$ at 50° C. or similar procedures employing similar low ionic strength and high temperature washing agents and similar denaturing agents.

The term "substance" means an element, compound, molecule, or a mixture thereof or any other material that could potentially be useful for diagnosing, prognosing, or modulating the onset or severity of an abnormal joint condition in an animal, including any drug, chemical entity, or biologic entity.

The term "siRNA" means a polynucleotide that forms a double stranded RNA that reduces or inhibits expression of a gene when the siRNA is expressed in the same cell as the gene. The term encompasses double stranded RNA formed by complementary strands. The siRNA complementary portions that hybridize to form the double stranded molecule typically have substantial or complete identity. Typically, siRNA contains at least about 15-50 nucleotides and the double stranded siRNA contains about 15-50 base pairs, preferably about 20-30 nucleotides and base pairs.

The term "specifically bind" means a special and precise interaction between two molecules which is dependent upon their structure, particularly their molecular side groups. For example, the intercalation of a regulatory protein into the major groove of a DNA molecule, the hydrogen bonding along the backbone between two single stranded nucleic acids, or the binding between an epitope of a protein and an agonist, antagonist, or antibody.

The term "specifically hybridize" means an association between two single stranded polynucleotides of sufficiently complementary sequence to permit such hybridization under predetermined conditions generally used in the art (sometimes termed "substantially complementary"). For example, the term may refer to hybridization of a polynucleotide probe with a substantially complementary sequence contained within a single stranded DNA or RNA molecule according to an aspect of the invention, to the substantial exclusion of hybridization of the polynucleotide probe with single stranded polynucleotides of non-complementary sequence.

The term "variant" means (1) a polynucleotide sequence containing any substitution, variation, modification, replacement, deletion, or addition of one or more nucleotides from or to a polynucleotide sequence and that has the same or substantially the same properties and performs the same or substantially the same function as the original sequence and (2) a polypeptide sequence containing any substitution, variation, modification, replacement, deletion, or addition of one or more amino acids from or to a polypeptide sequence and that has the same or substantially the same properties and performs the same or substantially the same function as the original sequence. The term therefore includes single nucleotide polymorphisms (SNPs) and allelic variants and includes conservative and non-conservative amino acid substitutions in polypeptides. The term also encompasses chemical derivatization of a polynucleotide or polypeptide and substitution of nucleotides or amino acids with nucleotides or amino acids that do not occur naturally, as appropriate.

The invention is not limited to the particular methodology, protocols, and reagents described herein because they may vary. Further, the terminology used herein is for the purpose of describing particular embodiments only and is not intended to limit the scope of the present invention. As used herein and in the appended claims, the singular forms "a," "an," and "the" include plural reference unless the context clearly dictates otherwise, e.g., reference to "a variant" includes a plurality of variants. Further, defined terms include variations of the terms used in the proper grammatical context, e.g., the term "specifically binds" includes "specific binding" and other forms of the term. Similarly, the words "comprise", "comprises", and "comprising" are to be interpreted inclusively rather than exclusively.

Unless defined otherwise, all technical and scientific terms and any acronyms used herein have the same meanings as commonly understood by one of ordinary skill in the art in the field of the invention. Although any compositions, methods, articles of manufacture, or other means or materials similar or equivalent to those described herein can be used in the practice of the present invention, the preferred compositions, methods, articles of manufacture, or other means or materials are described herein.

All patents, patent applications, publications, and other references cited or referred to herein are incorporated herein by reference to the extent allowed by law. The discussion of those references is intended merely to summarize the assertions made therein. No admission is made that any such patents, patent applications, publications or references, or any portion thereof, is relevant prior art for the present invention and the right to challenge the accuracy and pertinence of such patents, patent applications, publications, and other references is specifically reserved.

In one embodiment, the present invention encompasses one or more genes or gene segments ("genes" as defined herein) that are differentially expressed in abnormal animals compared to normal animals. The invention is based upon the discovery of polynucleotides that are differentially expressed in abnormal animals compared to normal animals. The genes were identified by comparing the expression of genes in lymphocytes from animals diagnosed as abnormal with genes in lymphocytes from animals diagnosed as normal using Affymetrix GeneChip® technology.

The polynucleotides and genes are identified by measuring differences in gene expression from lymphocytes from canines diagnosed as abnormal with gene expression in lymphocytes from canines diagnosed as normal. Changes in gene expression can be determined by any method known to skilled artisans. Generally, changes in gene expression are determined by measuring transcription (determining the amount of mRNA produced by a gene) or measuring translation (determining the amount of protein produced by a gene). The amount of RNA or protein produced by a gene can be determined using any method known to skilled artisans for quantifying polynucleotides and proteins. Generally, RNA expression is determined using polymerase chain reaction (PCR) (including, without limitation, reverse transcription-PCR (RT-PCR) and quantitative real-time PCR (qPCR)), RNase protection, Northern blotting, and other hybridization methods. The RNA measured is typically in the form of mRNA or reverse transcribed mRNA. Protein or polypeptide expression is determined using various colormetric and spectroscopic assays and methods such as the lowry assay, the biuret assay, fluorescence assays, turbidimetric methods, the bicinchoninic assay, protein chip technology, infrared absorbance, ninhydrin, the bradford assay, and ultraviolet absorbance. In a preferred method, changes in gene expression are determined using Affymetrix Canine-1 and Canine-2 gene chips available for purchase from Affymetrix, Inc. and the instructions for using such chips to determine gene expression.

Generally, differential gene expression in abnormal animals compared to normal animals is determined by measuring the expression of at least one gene. Preferably, the expression of two or more differentially expressed genes is measured to provide a gene expression pattern or gene expression profile. More preferably, the expression of a plurality of differentially expressed genes is measured to provide additional information for a more significant gene expression pattern or profile.

In another aspect, the invention provides a device suitable for detecting the expression of a plurality of genes differentially expressed in abnormal animals compared to normal animals. The device comprises a substrate having a plurality of the oligonucleotide or polynucleotide probes of the present invention affixed to the substrate at known locations. The device is essentially an immobilized version of the oligonucleotide or polynucleotide probes described herein. The device is useful for rapid and specific detection of genes and polynucleotides and their expression patterns and profiles. Typically, such probes are linked to a substrate or similar solid support and a sample containing one or more polynucleotides (e.g., a gene, a PCR product, a ligase chain reaction (LCR) product, a DNA sequence that has been synthesized using amplification techniques, or a mixture thereof) is exposed to the probes such that the sample polynucleotide(s) can hybridize to the probes. Either the probes, the sample polynucleotide(s), or both, are labeled, typically with a fluorophore or other tag such as streptavidin, and detected using methods known to skilled artisans. If the sample polynucleotide(s) is labeled, hybridization may be detected by detecting bound fluorescence. If the probes are labeled, hybridization is typically detected by label quenching. If both the probe and the sample polynucleotide(s) are labeled, hybridization is typically detected by monitoring a color shift resulting from proximity of the two bound labels. A variety of labeling strategies and labels are known to skilled artisans, particularly for fluorescent labels. Preferably, the probes are immobilized on substrates suitable for forming an array (known by several names including DNA microarray, gene chip, biochip, DNA chip, and gene array) comparable to those known in the art.

The polypeptide probes may be made according to conventional methods, e.g., using the nucleotide sequence data provided for polynucleotides of the present invention and methods known in the art. Such methods include, but are not limited to, isolating polypeptide directly from cells, isolating or synthesizing DNA or RNA encoding the polypeptides and using the DNA or RNA to produce recombinant products, synthesizing the polypeptides chemically from individual amino acids, and producing polypeptide fragments by chemical cleavage of existing polypeptides.

In another aspect, the invention provides a device suitable for detecting the expression of a plurality of genes differentially expressed in abnormal animals compared to normal animals. The device comprises a substrate having a plurality of the peptide or polypeptide probes of the present invention affixed to the substrate at known locations. The device is essentially an immobilized version of the peptide or polypeptide probes described herein. The device is useful for the rapid and specific detection of proteins and their expression patterns. Typically, such probes are linked to a substrate and a sample containing one or more proteins is exposed to the probes such that the sample proteins can hybridize to the probes. In certain embodiments, the probes, the sample proteins, or both, are labeled and detected, typically with a fluorophore or other agent known to skilled artisans. Generally, the same methods and instrumentation used for reading polynucleotide microarrays is applicable to protein arrays. Preferably, the probes are immobilized on a substrate suitable for forming an array.

Methods for determining the amount or concentration of protein in a sample are known to skilled artisans. Such methods include radioimmunoassays, competitive-binding assays, Western blot analysis, and ELISA assays. For methods that use antibodies, polyclonal and monoclonal antibodies are suitable. Such antibodies may be immunologically specific for a protein, protein epitope, or protein fragment.

Some embodiments of the invention utilize antibodies for, the detection and quantification of proteins produced by expression of the polynucleotides of the present invention. Although proteins may be detected by immunoprecipitation, affinity separation, Western blot analysis, protein arrays, and the like, a preferred method utilizes ELISA technology wherein the antibody is immobilized on a solid support and a target protein or peptide is exposed to the immobilized antibody. Either the probe, or the target, or both, can be labeled using known methods.

In some embodiments, expression patterns or profiles of a plurality of genes differentially expressed in abnormal animals compared to normal animals are observed utilizing an array of probes for detecting polynucleotides or polypeptides. In one embodiment, arrays of oligonucleotide or polynucleotide probes may be utilized, whereas another embodiment may utilize arrays of antibodies or other proteins that specifically bind to the differentially expressed gene products of the present invention. Such arrays may be commercially available or they may be custom made using methods known to skilled artisans, e.g., in-situ synthesis on a solid support or attachment of pre-synthesized probes to a solid support via micro-printing techniques. In various embodiments, arrays of polynucleotides or polypeptides probes are custom made to specifically detect transcripts or proteins produced by the differentially expressed genes of the present invention.

In one embodiment, arrays of polynucleotide or polypeptide probes are custom made to specifically detect transcripts or proteins produced by two or more polynucleotides or genes identified, in Table 2 and/or Table 3. These probes are designed to detect genes associated with lipid and glucose metabolism pathways in animals. In another embodiment, arrays of polynucleotide or polypeptide probes are custom made to specifically detect transcripts or proteins produced by two or more polynucleotides or genes identified in Table 3. These probes are designed to detect genes that are particularly relevant to abnormal animals compared to normal animals.

In a further aspect, the invention provides a method for detecting the differential expression of one or more genes differentially expressed in abnormal animals compared to normal animals in a sample. The method comprises (a) hybridizing a combination comprising a plurality of polynucleotide probes that are differentially expressed in abnormal animals compared to normal animals with polynucleotides in the sample to form one or more hybridization complexes; (b) optionally, hybridizing a combination comprising a plurality of polynucleotide probes that are differentially expressed in abnormal animals compared to normal animals with polynucleotides in a standard to form one or more hybridization complexes; (c) detecting the hybridization complexes from the sample and, optionally, the standard from step (b); and (d) comparing the hybridization complexes from the sample with the hybridization complexes from a standard, wherein a difference in the amount of hybridization complexes between the standard and sample indicate differential expression of genes differentially expressed in abnormal animals compared to normal animals in the sample.

Step (b) and part of step (c) are optional and are used if a relatively contemporaneous comparison of two or more test systems is to be conducted. However, in a preferred embodiment, the standard used for comparison is based upon data previously obtained using the method.

These probes are exposed to a sample to form hybridization complexes that are detected and compared with those of a standard. The differences between the hybridization complexes from the sample and standard indicate differential expression of polynucleotides and therefore genes differentially expressed in abnormal animals compared to normal animals in the sample. In a preferred embodiment, probes are made to specifically detect polynucleotides or fragments thereof produced by one or more of the genes or gene fragments identified by the present invention. Methods for detecting hybridization complexes are known to skilled artisans.

In one embodiment, the method further comprises exposing the animal or sample to a test substance before hybridization. Then, the comparison is indicative of whether the test substance altered the expression of genes differentially expressed in abnormal animals compared to normal animals, particularly abnormal-associated genes, in the sample.

In another aspect, the invention provides a method for detecting the differential expression of genes differentially expressed in abnormal animals compared to normal animals in a sample. The method comprises (a) reacting a combination comprising a plurality of polypeptide probes with proteins in the sample under conditions that allow specific binding between the probes and the proteins to occur, wherein the proteins bound by the probes are differentially expressed in a abnormal animal compared to a normal animal; (b) optionally, reacting a combination comprising a plurality of polypeptide probes with proteins in a standard under conditions that allow specific binding between the probes and the proteins to occur, wherein the proteins bound by the probes are differentially expressed in a abnormal animal compared to a normal animal; (c) detecting specific binding in the sample and, optionally, the standard from step (b); and (d) comparing the specific binding in the sample with that of a standard, wherein differences between the specific binding in the standard and the sample indicate differential expression of genes differentially expressed in abnormal animals compared to normal animals in the sample.

These probes are exposed to a sample to form specific binding that is detected and compared with those of a standard. The differences between the specific binding from the sample and standard indicate differential expression of proteins and therefore genes differentially expressed in abnormal animals compared to normal animals, particularly abnormal-associated genes, in the sample. In a preferred embodiment, probes are made to specifically detect proteins or fragments thereof produced by one or more of the genes or gene fragments identified by the present invention.

In one embodiment, the method further comprises exposing the animal or sample to a test substance before reacting the polypeptides with the proteins. Then, the comparison is indicative of whether the test substance altered the expression of genes differentially expressed in abnormal animals compared to normal animals, particularly abnormal-associated genes, in the sample.

In another aspect, the method for detecting the expression of genes differentially expressed in abnormal animals compared to normal animals in a sample is used to monitor an animal's progress when attempting to modulate the amount of, for example, arthritis, tissue on the animal in response to a cartilage tissue modulation program. The method is performed at intervals, preferably set intervals, during the modulation program and the animal's progress monitored by comparing the results of the method at two or more points during the modulation program. A change in expression of one or more of the genes differentially expressed in abnormal animals compared to normal animals, particularly abnormal-associated genes, or in the pattern of gene expression, or the lack of any change, resulting from the comparison indicates the effectiveness of the modulation program.

Test substances can be any substance that may have an effect on polynucleotides or genes differentially expressed in abnormal animals compared to normal animals, particularly abnormal-associated genes. Test substances include, but are not limited to, amino acids; proteins, peptides, polypeptides, nucleic acids, oligonucleotides, polynucleotides, small molecules, macromolecules, vitamins, minerals, simple sugars; complex sugars; polysaccharides; carbohydrates; medium-chain triglycerides (MCTs); triacylglycerides (TAGs); n-3 (omega-3) fatty acids including DHA, EPA, ALA; n-6 (omega-6) fatty acids including LA, γ-linolenic acid (GLA) and ARA; SA, conjugated linoleic acid (CLA); choline sources such as lecithin; fat-soluble vitamins including vitamin A and precursors thereof such as carotenoids (e.g., β-carotene), vitamin D sources such as vitamin D2 (ergocalciferol) and vitamin D3 (cholecalciferol), vitamin E sources such as tocopherols (e.g., α-tocopherol) and tocotrienols, and vitamin K sources such as vitamin K1 (phylloquinone) and vitamin K2 (menadione); water-soluble vitamins including B vitamins such as riboflavin, niacin (including nicotinamide and nicotinic acid), pyridoxine, pantothenic acid, folic acid, biotin and cobalamin; and vitamin C (ascorbic acid); antioxidants, including some of the vitamins listed above, especially vitamins E and C; also bioflavonoids such as catechin, quercetin and theaflavin; quinones such as ubiquinone; carotenoids such as lycopene and lycoxanthin; resveratrol; and α-lipoic acid; L-carnitine; D-limonene; glucosamine; S-adenosylmethionine; and chitosan. In a preferred embodiment, test substances are nutrients that may be added to food or consumed as a supplement. Examples include, but are not limited to, fatty acids such as omega-3 fatty acids (e.g., DHA and EPA) and omega-6 fatty. acids (e.g., ARA), carnitine, methionine, vitamin C, vitamin E, and vitamin D.

In a preferred embodiment, the substances useful for affecting the expression of genes differentially expressed in abnormal animals compared to normal animals, particularly abnormal-associated genes, may be identified using methods discloses in co-pending U.S. Provisional Patent Application No. 60/657980, filed Mar. 2, 2005, and any subsequent US or foreign patent application that claims priority thereto.

The expression profile for normal animals used in the comparison can be obtained from one or more normal animals contemporaneously with the expression profile for the animal being tested of from a database of normal animal expression profiles. Preferably, a database of expression profiles for normal animals accumulated over time is available for use as a reference.

Determining if the polynucleotides or polypeptides are differentially expressed can be accomplished by detecting the polynucleotides or polypeptides using methods known to skilled artisans, some of which are described herein.

In another aspect, the invention provides a composition suitable for manipulating the genome of an animal. The composition comprises one or more substances that interfere with the expression of one or more genes differentially expressed in abnormal animals compared to normal animals, particularly abnormal-associated genes.

In another embodiment, the invention encompasses a method for modulating the expression of one or more genes differentially expressed in animals having abnormal musculoskeletal joint disorders compared to normal animals, particularly abnormal musculoskeletal joint disorder-associated genes. In preferred embodiments the composition comprises, in milligrams per kilogram of body weight per day (mg/kg/day), DHA in amounts of from about 1 to about 30, preferably from about 3 to about 15; EPA in amounts of from about 1 to about 30, preferably from about 3 to about 15; EPA/DHA Combo (1.5:1 ratio) in amounts of from about 4/2 to about 30/45, preferably from about 9/6 to about 18/12; ALA in amounts of from about 10 to about 100, preferably from about 30 to about 60; LA in amounts of from about 30 to about 600, preferably from about 60 to about 300; ARA in amounts of from about 5 to about 50, preferably from about 15 to about 30; SA in amounts of from about 3 to about 60, preferably from about 6 to about 30; and CLA (as a control) in amounts of from about 6 to about 120, preferably from about 12 to about 60. The composition can be administered to the animal in any manner or form suitable for the composition. Preferably, the composition is administered to the animal orally in the form of a food composition or a supplement. The food composition may be of any form, e.g., a nutritionally balanced food composition known in the art such as dry foods, semi-moist foods, and wet foods for animals, particularly companion animals such as feline and canine animals. Supplements include dosage forms such as tablets, capsules, and similar forms. In a further aspect, the composition is administered in combination with one or more drugs or other substances that modulate the amount of cartilage tissue in an animal.

In another aspect, the invention provides a composition suitable for modulating the expression of one or more genes differentially expressed in animals having abnormal musculoskeletal joint disorders compared to normal animals, particularly abnormal musculoskeletal joint disorder-associated genes, or modulating the amount of cartilage tissue in an animal. The composition comprises a gene expression or tissue modulating amount of one or more of DHA, EPA, EPA and DHA, ALA, LA, ARA, and SA. In various embodiments, the composition comprises, in mg/kg/day, DHA in amounts sufficient to administer to an animal from about 1 to about 30; EPA in amounts sufficient to administer to an animal from about 1 to about 30; EPA/DHA Combo (1.5:1 ratio) in amounts sufficient to administer to an animal from about 4/2 to about 30/45; ALA in amounts sufficient to administer to an animal from about 10 to about 100; LA in amounts sufficient to administer to an animal from about 30 to about 600; ARA in amounts sufficient to administer to an animal from about 5 to about 50; SA in amounts sufficient to administer to an animal from about 3 to about 60; and CLA (as a control) in amounts sufficient to administer to an animal from about 6 to about 120. Such substances may be useful for modulating the amount of cartilage tissue in an animal. Preferably, the substances affect the expression of a plurality of such genes. In one embodiment, the composition further comprises one or more drugs or other substances that modulate the amount of cartilage tissue in an animal.

In a further aspect, the present invention provides kits suitable for determining the differential expression of one or more genes differentially expressed in animals having abnormal musculoskeletal joint disorders compared to normal animals, particularly abnormal musculoskeletal joint disorder-associated genes, in a test system.

Example 1: Determining the Effect of Various Substances or Ingredients on Gene Expression in Canine Cell Lines Affymetrix canine gene chips Canine Genome-1 and Canine Genome-2 are used to determine the effect of various test substances or ingredients such as MCTs; TAGs; ALA; EPA; DHA; linoleic acid; stearic acid (SA), conjugated linoleic acid (CLA), GLA; arachidonic acid; lecithin; vitamin A, vitamin D, vitamin E, vitamin K, riboflavin, niacin, pyridoxine, pantothenic acid, folic acid, biotin vitamin C, catechin, quercetin, theaflavin; ubiquinone; lycopene, lycoxanthin; resveratrol; α-lipoic acid; L-carnitine; D-limonene; glucosamine; S-adenosylmethionine; chitosan, various materials containing one or more of these compounds, and various combination thereof on gene expression in four canine cell lines and appropriate controls. Each ingredient is tested in two concentrations as illustrated for selected sample ingredients shown in Table 1. The solvent at the higher of the two concentrations is used as a control. Four canine cell lines are used: CCL34 (kidney), CRL1430 (thymus), CCL183 (bone) (obtained from The American Tissue Culture Collection) and CTAC (thyroid) (See, Measurement of NK Activity in Effector Cells Purified from Canine Peripheral Lymphocytes, Veterinary Immunology and Immunopathology, 35 (1993) 239-251). A cell line treated with an ingredient at a specific concentration is referred to as "treatment" and an untreated sample is referred to as "control." The words "genes" and "probes" are used synonymously in this method. Gene expression is measured for the treatment cell lines and controls using the instructions provided with the Affymetrix chips. Detailed sequence information for each unique probe identification number is available from the manufacturer.

The gene expression data is determined to be either "up" or "down" -regulated for any given treatment. The decision on whether a gene is "up" or "down" is based on the fold change, which is calculated as treatment intensity/control intensity for each individual probe. The fold change is considered down-regulated if its value is <1/1.5 (for across all 4 cell lines analysis) or <1/2 (for within cell lines analysis) and is up-regulated if it is >1.5 (for across all 4 cell lines analysis) or >2 (for within cell lines analysis). Also, a probe is considered significant for further scrutiny if it is called as present in only one of the conditions being compared (treatment or control) and is "absent" or "marginal" in the other and the fold change is significant according to the software used. Probes that appear to be regulated in opposite directions in the two treatments are excluded from further analysis.

The raw data is analyzed using GeneSpring version 7.0 (GS) software (Agilent Corporation) and validated using the R-Bioconductor (RB) freeware. Both software packages are used to compute probe intensities from the CEL files generated by the Affymetrix Instrument. The Present/Absent/Marginal calls per probe and P-values are computed using the R-Bioconductor and GeneSpring software separately.

Two schemes are used for data analysis. First; "across cell lines" and "within individual cell lines." In the first scheme, genes are selected for scoring provided they are found to be significant and common across all cell-lines. The "across cell lines" yields the highest confidence data with minimum noise and may provide the best possible clues as to which genes are affected by individual ingredients. In the second scheme, only those genes that show a significant fold change in the two treatments according to both software packages within an individual cell lines are scored. A sample of the data obtained from these experiments is shown in Table 2. Table 2 shows the correlation between treatment substance (Column 1), Probe (data link) (Column 2), Direction (Column 3), Best BLAST Annotation (determined statistically) (Column 4), and Human Accession Number (Column 5). The information for all ingredients tested is stored in a database for reference.

Based upon the physiological condition of the canines (a diagnosis as abnormal) and a comparison of the information from the Tables 1-2, i.e, noting genes that are influenced by a test substance or ingredient and are also differentially expressed in abnormal canines compared to normal canines, a nutritional formula useful for selecting and preparing a food composition for abnormal canines would be believed to contain one or more of the following ingredients in the following amounts (in vivo amounts in milligrams per kilogram of body weight per day (mg/kg/day) are based upon extrapolation from amounts used in vitro, for example: DHA—from about 1 to about 30; EPA—from about 1 to about 30; EPA/DHA Combo (1.5:1 ratio)—from about 4/2 to about 30/45; ALA—from about 10 to about 100; LA—from about 30 to about 600; ARA—from about 5 to about 50; and SA—from about 3 to about 60. Based upon these data, a food composition and related diet containing one or more of these ingredients can be prepared and used to regulate the genes that are differentially expressed in abnormal animals compared to normal animals. Such regulation will cause the modulation of abnormal musculoskeletal joint disorders in the animal and, therefore, in one embodiment, promote a shift to a desirable or normal status and promote better health and wellness of the animal.

Example 2: RNA Isolation Procedures

Materials and Methods. The following general procedures may be used to isolate RNA from tissue samples of dogs and cats for gene expression profiling utilizing gene chips as further described in the Examples of this specification. It will be apparent to a person of ordinary skill in the art that these procedures or modifications thereof as recognized within the art can be applied to isolate RNA from tissue or body fluid samples for further gene expression analysis using a variety of analytical procedures available to a person of ordinary skill in the art, in particular microarray technologies.

Isolation of Ribonucleic Acid (RNA) from Tissue

Tissue samples may be collected, frozen in liquid nitrogen, thawed and then homogenized and processed using a TRIzol® RNA extraction method to produce good quality RNA which is then subjected to further genomic analysis.

Materials: ice, liquid nitrogen, frozen canine or feline tissue, TRIzol® lysis reagent, chloroform minimum 99%, isopropyl alcohol, 70% ethanol (prepared with ethanol, absolute and deionized, RNase-free water), RNase Zap®, deionized water, RNA Storage Solution®, from Ambion.

Equipment: Ultra-Turrax T25 Power Homogenizer, Beckman Coulter Allegra 25R Centrifuge, Eppendorf Centrifuge, forceps, scalpel, hard cutting surface, i.e. cutting board, 1.5 mL DNase and RNase free/sterile microcentrifuge tubes, 50 mL DNase and RNase free/sterile disposable polypropylene tubes, P1000, P200, P20, P10 and P2 Rainin Pipetman pipettes, filter pipette tips for P1000, P200, P20, P10 and P2 pipettes, DNase and RNase free/sterile, and lint free wipes.

Preparations: Prepare 50 mL polypropylene tubes with 4 mL TRIzol® (one tube for each tissue selected for RNA isolation).

Tissue Homogenization: Fill a container capable of holding liquid nitrogen with 3-4 scoops of liquid nitrogen. Place a piece of frozen tissue immediately into the aforementioned container (the tissue should be about the size of a pea) and place the tissue into the appropriate labeled 50 mL polypropylene tube (that already contains 4 mL TRIzol®). Immediately begin homogenization using the Ultra-Turrax T25 Power Homogenizer. Homogenize on the highest setting (6) for 10-15 seconds. Cool the sample on ice for another 10-15 seconds and then repeat. Continue until the tissue is fully homogenized and the solution is cloudy. Upon complete homogenization, cap the 50 mL tube and return to the ice. Incubate the homogenized tissues at room temperature for 5 minutes before proceeding with the isolation procedure.

Example 3: RNA Preparation Procedures

RNA Isolation: The procedures given in the Invitrogen instructions provided with the TRIzol® reagent are generally followed. Separate the homogenized sample into four 1 mL aliquots in four 1.5 mL microcentrifuge tubes. Add 200 µL of chloroform to each 1 mL aliquot. Cap the tubes, vortex for 15 seconds and then shake up and down. The result should be a pink milky liquid. Incubate the tubes at room temperature for 2-3 minutes. Centrifuge the tubes for 15 minutes at 14,000 rpm and 4° C. Transfer the aqueous phase (top layer) to a sterile 1.5 mL microcentrifuge tube. The typical volume of the aqueous phase which should be transferred to the new tube is about 500 uL. Be sure not to transfer any of the intermediate or lower phase. Precipitate the RNA from solution by adding 500 uL of Isopropyl Alcohol to each microcentrifuge tube containing the aqueous layer. Shake the tubes up and down for at least 20 seconds. Incubate the samples at room temperature for 10 minutes. Centrifuge the samples for 10 minutes, 14,000 rpm at 4° C. Remove the supernatant carefully by aspirating off the liquid being sure not to lose the pellet. Add 1 mL of 70% ethanol to wash the pellet. Dislodge the pellet by flicking the tube (or tapping the tube on the bench top) and shake to mix. Centrifuge for 5 minutes, 8,200 rpm at 4° C. Remove the supernatant carefully by aspirating off the liquid being sure not to lose the pellet. Using a lint free wipe to carefully soak up excess ethanol to make sure the pellet is dry. Resuspend each pellet into 30 uL of RNA Storage Solution. Mix gently by pipetting until the RNA goes back into solution and then store at −80° C. It may be necessary to vortex the sample for a few seconds at a low speed to facilitate the resuspension of the RNA. If this is necessary, spin down the samples, using the microcentrifuge, prior to freezing.

RNA Cleaning: The procedures given in the RNeasy® Mini Handbook are followed.

RNA Isolation from Cells Cultured in OptiCell Chambers Using the RNeasy Mini Kit.

Cells cultured from mammalian cell lines are used to isolate good quality RNA which is then used for future downstream genomic analysis. All work related to the culturing of the cells is to be done under strict aseptic conditions.

Reagents: 10×PBS, deionized $H_2O$, absolute ethanol, RNA Storage Solution, β-Mercaptoethanol, RNase Zap®, Buffer RLT, and Buffer RWI and Buffer RPE (provided in the RNeasy Mini Kit)

Equipment/Materials: RNeasy Mini Kit, QIAshredder spin columns, OptiCell knife, 20 mL sterile syringe, OptiCell tips, Cell scraper, P1000 Pipetman pipette, Rainin, P200 Pipetman pipette, Rainin, 100-100 uL filtered pipette tips, 1-200 uL filtered pipette tips, sterile transfer pipettes, 55 mL sterile solution basin, 1.5 mL sterile microcentrifuge tubes, and Eppendorf Microcentrifuge.

Solutions: Buffer RLT (stock provided in RNeasy Mini Kit); -Add 100 uL of β-Mercaptoethanol per 10 mL of Buffer RLT prior to beginning protocol. 70% Ethanol: Make 50 mL of 70% ethanol by adding 35 mL absolute ethanol to 15 mL deionized, RNase-free water. 1×PBS: RNase-free water. Filter the solution using a 22um filter.

Procedure: Removing Cells from the OptiCell Chamber (proceed one OptiCell at a time). Check the cells under a microscope to ensure that the cells are alive before isolating RNA. Remove and discard the cell culture medium. Using the OptiCell knife, cut away the top membrane exposing the cells on the lower membrane. Wash the membrane to which the cells are attached three times with 1×PBS. Pipette 600 uL of the Buffer RLT solution (containing β-Mercaptoethanol) onto the center of the membrane to which the cells are attached. Using the cell scraper, gently spread the Buffer RLT over the entire surface of the membrane, and then collect the liquid in one corner. Pipette off the entire volume of Buffer RLT and place into a QIAshredder spin column.

RNA Isolation: Centrifuge the QIAshredder spin columns at 14,000 rpm for 2 minutes. Discard the spin column but keep the collection tube and its contents. Add 600 uL of 70% ethanol to the collection tube and mix well by pipetting (the total volume now=1.2 mL). Transfer 600 uL of the cell lysate to an RNeasy mini column and centrifuge for 15 seconds at 14,000 rpm. Discard the flow through but keep the collection tube and the spin column. Transfer the remaining volume of cell lysate (~600 uL) to the spin column and repeat the centrifugation. Discard the flow through but keep the collection tube and the spin column. Add 700 uL Buffer RW I to the spin column. Centrifuge for 15 seconds at 14,000 rpm to wash the column. Discard the flow through and the collection tube. Transfer the spin column to a new 2 mL collection tube and add 500 uL Buffer RPE to the column. Centrifuge for 15 seconds at 14,000 rpm. Discard the flow through, keep the collection tube/column. Add another 500 uL Buffer RPE to the column. Centrifuge for 2 minutes at 14,000 rpm. Transfer the spin column to a 1.5 mL collection tube. Add 30 uL of RNA Storage Solution directly to the silica gel membrane and centrifuge for 1 minute at 14,000 rpm to elute the RNA. Store the final RNA at −70° C.

RNA 6000 Nano Assay

Using the Agilent 2100 Bioanalyzer and the RNA 6000 Nano Assay, analyze RNA isolated from cultured mammalian cells, lymphocytes or tissues for quality.

Reagents: RNA 6000 Nano gel matrix, RNA 6000 Nano dye concentrate, RNA 6000 Nano Marker, (all of the above reagents are contained in the RNA 6000 Nano Assay kit, Agilent), RNA 6000 ladder, RNase Zap, and RNase-free water, from Ambion.

Equipment/Other Materials: Agilent Chip Priming Station, Agilent, RNA 6000 chip, Agilent, electrode cleaners, P2, P10, P200, and P1000 Rainin Pipetman pipettes, sterile, DNase/RNase free filtered pipette tips, 1.5 mL microcentrifuge tubes, sterile, vortex, IKA vortex mixer, microcentrifuge, and heating block.

Procedure: The procedure is given in the Reagent Kit Guide, RNA 6000 Nano Assay, Edition November 2003, by Agilent Technologies. The procedures are followed as given in the Guide, with the following modifications: Preparing the Gel, pg. 17—rather than separating the filtered gel into aliquots of 65 uL each, keep the stock filtered gel in the original microcentrifuge tube and aliquot the 65 uL as needed. Loading the RNA 6000 Nano Marker, pg. 22—add 1 uL of RNase-free water (instead of RNA 6000 Nano Marker) to each sample well that will not contain sample. Not only will this conserve the amount of Marker used but also serves as a negative control to see that none of the reagents are contaminated, including the RNase-free water. Loading the Ladder and Samples, pg. 23—heat denature the samples and RNA 6000 Ladder for an additional 30 seconds (total of 2.5 minutes) at 71° C. Starting the Chip Run, pg. 26—choose the "Eukaryote Total RNA Nano" option from the assay menu.

Example 4: Affymetrix GeneChip Expression Analysis

Gene expression is analyzed using Affymetrix Canine 1 and Canine 2 GeneChip®. Arrays which are commercially available from Affymetrix, Inc., Santa Clara, Calif. 95051. Total RNA is reverse transcribed into cDNA. The cDNA is used to generate cRNA which is fragmented and used as probes for GeneChip hybridization. The gene chip is washed and the hybridization signal is measured with an Affymetrix laser scanner. The hybridization data is then validated and normalized for further analysis.

Materials: Affymetrix provides most of the reagents and kit. Other reagents listed in the Affymetrix Manual but not supplied in the kit may be obtained separately (refer to GeneChip Expression Analysis Technical Manual (701021 Rev.4) for details), RNase Zap® and deionized water.

Equipment: Eppendorf microcentrifuge, 1.5 mL DNase and RNase free/sterile microcentrifuge tubes, 50 mL DNase and RNase free/sterile disposable polypropylene tubes, P1000, P200, P20, P10 and P2 Rainin Pipetman pipettes, Filter pipette tips for P1000, P200, P20, P10 and P2 pipettes, DNase and RNase free/sterile, and Peltier Thermal Cycler PTC-200.

Procedure: follow all procedures exactly as described in GeneChip Expression Analysis Technical Manual (Affymetrix Copyright 1999-2003). Use 5 microgram of total RNA for the first strand cDNA synthesis. Use either Peltier Thermal Cycler PTC-200 or heat block for temperature control on reactions and probe denaturing. The quality control is performed using RNA NanoDrop chips with BioAnalyzer 2100. Use 100 Format (Midi Array) for the canine genechip.

Example 5: Assay Procedures in Cats

Whole blood is obtained from the cats in the studies provided herein using PAXgene™ RNA tubes and total RNA is isolated from whole blood samples using PAXgene™ RNA isolation kit according to the methods detailed below.

PAXgene™ Blood RNA Isolation: PAXgene™ Blood RNA tubes and the PAXgene™ Blood RNA Kit (Qiagen) are used together to isolate and purify intracellular RNA from whole blood obtained from felines as provided below (see also PAXgene™ Blood RNA Kit Handbook, PreAnalytix, June 2005). Briefly, blood is collected using a Vacutainer® needle, directly into the PAXgene™ Blood RNA tube and then subjected to several rounds of centrifugation, wash and purification steps which ultimately result in high-quality RNA. The RNA then undergoes a quality control step and is then used in future quantitative real-time PCR and/or microarray analyses using a custom manufactured proprietary feline gene chip produced on the Affymetrix platform.

Assay Preparations: Incubate PAXgene™ tubes (containing blood) for at minimum of 2 hours at room temperature before beginning the assay. If the tubes are frozen, and are not allowed to incubate for 2 hours prior to freezing, they will need to sit at room temperature to thaw an additional 2 hours. Invert each PAXgene™ tube 8-10 times before the first centrifugation. If using Buffer BR4 (buffers are included with the PAXgene™ Blood RNA Kit) for the first time, add 4 volumes of 96-100% ethanol to the concentrated buffer to obtain a working solution. Preheat two heating blocks prior to beginning the assay—65° C. and 55° C. Prepare the DNase I stock solution (the RNase-Free DNase Set is included with the PAXgene™ Blood RNA Kit). Dissolve the solid DNase I enzyme in 550 μL, of RNase-free water provided with the kit. Be sure not to lose any DNase I when removing the lid. Mix gently by inverting the tube. Do not vortex or centrifuge. Make a mixture of DNase I enzyme and Buffer RDD (kit component) (enough volume for the number of samples being processed per batch). Each sample needs 70 μL of Buffer RDD and 10 μL of DNase I (i.e. 20 samples would require a cocktail of 1.4 mL Buffer RDD and 200 μL DNase I). The cocktail should be stored at 2-8° C. until needed. The reconstituted enzyme is good for up to 6 weeks at 2-8° C.

Sample storage: PAXgene™ tubes (which contain blood) can be stored at room temperature for up to 3 days before processing. According to the product insert provided with the PAXgene™ Blood RNA tubes, the cellular RNA profile is stable under these conditions for up to 3 days. This, however, may vary between species. PAXgene™ tubes can also be stored at 4° C. for up to 5 days. If long term storage is required, PAXgene™ tubes can be stored at −20° C. or −70° C. for up to 6 months. Tubes should be frozen in a loose wire rack in an upright position. It is recommended to freeze first at −20° C. and then transfer to −70° C. if tubes will be stored at −70° C. Upon removing the tubes from the freezer they should be thawed at room temperature (temperature not to exceed 22° C.). Each tube is to be inverted 10 times before proceeding with the assay.

RNA Isolation from Whole Blood: Centrifuge the PAXgene™ Blood RNA tubes at 4000×g for 10 minutes. Remove the supernatant by decanting and discard. Blot excess supernatant remaining on rim of PAXgene™ tube. Add 4 mL of RNase-free water to the pellet and cap with a new Hemogard closure. Resuspend the pellet by vortexing and then centrifuge at 4000×g for 10 minutes. Remove the supernatant by decanting and discard. Blot excess supernatant remaining on rim of PAXgene™. Add 360 μL of Buffer BR1 (kit component) to the pellet and gently pipette until pellet is completely resuspended. Transfer the sample to a sterile 1.5 mL microcentifuge tube and add 300 μL Buffer BR2 (kit component) and 404 Proteinase K (do not mix Buffer BR2 and Proteinase K prior to adding to the sample). Mix each tube thoroughly by vortexing and place into a thermomixer preheated to 55° C. Incubate/shake the tubes for 10 minutes at 1400 rpm. Pipet the lysate into a QIAshredder spin column placed into a 2 mL collection tube. Centrifuge at 14,000 rpm for 3 minutes. Transfer the supernatant of the flow-through fraction to a sterile 1.5 mL microcentrifuge tube. Add 350 μL of 96-100% ethanol and gently mix by pipetting. Add 700 μL of the sample to the PAXgene™spin column placed in a 2 mL collection tube and centrifuge at 14,000 rpm for 1 minute. Transfer the PAXgene™ spin column into a new 2 mL collection tube and discard the flow-through and old collection tube. Add the remaining volume of the sample to the PAXgene™ spin column. Centrifuge at 14,000 rpm for 1 minute.

Discard the old collection tube and the flow-through from the centrifugation of the spin column described immediately above. Place the PAXgene™ spin column into a new 2 mL collection tube. Add 350 μL of Buffer BR3 (kit component) to the PAXgene™ spin column and centrifuge at 14,000 rpm for 1 minute. Discard the flow-through and collection tube. Place the column into a new 2 mL collection tube and add 80 μL of the DNase I/Buffer RDD cocktail (see "Assay Preparations") directly to the column membrane and incubate for 15 minutes at room temperature. Add another 350 μL Buffer BR3 to the PAXgene™ spin column. Centrifuge at 14,000 rpm for 1 minute. Transfer the PAXgene™ spin column to a new 2 mL collection tube and discard the old collection tube and flow-through.

Add 500 μL of Buffer BR4 (kit component) to the PAXgene™ spin column. Centrifuge at 14,000 rpm for 1 minute. Place the PAXgene™ spin column into a new 2 mL collection tube and discard the old collection tube and flow-through. Add another 500 μL Buffer BR4 to the PAXgene™ spin column. Centrifuge at 14,000 rpm for 3 minutes to dry the spin column membrane. Discard the collection tube and flow-through and place the columns in another 2 mL collection tube. Spin the samples again at 14,000 rpm for an additional minute to further dry the column membrane. Discard the flow-through and the collection tube. Transfer the PAXgene™ spin column to a 1.5 mL elution tube. Add 40 μL Buffer BR5 (kit component) directly to the PAXgene™ spin column membrane. Centrifuge at 14,000 rpm for 1 minute. Remove the PAXgene™ spin column and pipette the eluate in the 1.5 mL tube onto the same PAXgene™ spin column. Return the PAXgene™ spin column to the same 1.5 mL elution tube and centrifuge at 14,000 rpm for 1 minute. Incubate the final eluate at 65° C. for 5 minutes and immediately chill on ice. Store final RNA sample at −80° C. for future use.

Example 6: Gene Expression in Cats with Osteoarthritis Compared to Control Cats

Studies are conducted in accordance with Example 5 using non-arthritic cats and cats with osteoarthritis to determine the underlying gene expression differences between non-arthritic cats and cats with osteoarthritis. In a first study, a baseline comparison is performed between the two groups of cats to determine the underlying gene expression differences between non-arthritic cats and cats with osteoarthritis. Procedures as generally described in the Examples of this specification may be used to prepare tissue and bodily fluid samples.

With regard to the studies provided herein, cats with osteoarthritis are graded according to a previously published method, i.e., all non-arthritic cats are "grade 0" indicating that the joint appears to be normal, cats with osteoarthritis have grades that are either 1 (small enthesophytes or small osteophytes present) or 2 (more prominent enthesophytes and osteophytes). Cats with severe osteoarthritis (grade 3) are not included in this study.

A proprietary, custom made feline gene chip (Affymetrix) is used to evaluate base line gene expression in cats with and without osteoarthritis (10 normals, 10 arthritic animals). As provided above, gene chip analyses are performed using conventional methods and according to the manufacturer's instructions in order to obtain a baseline comparison between the two groups to determine the underlying gene expression differences between non-arthritic cats and cats with osteoarthritis.

The raw gene chip data is normalized using the Robust Multiarray Average (RMA) normalization algorithm (Irizarry, et al., Biostatistics 2003 Vol 4, Page 249-264) and is then subjected to statistical analysis using Support Vector Machine (SVM) algorithm (Partek Genomic Suite, Version 6) to determine the gene expression differences that can differentiate between arthritic and non-arthritic animals. Genes identifying OA biomarkers are selected based on p value cut off and fold change (FC).

Figure 3:
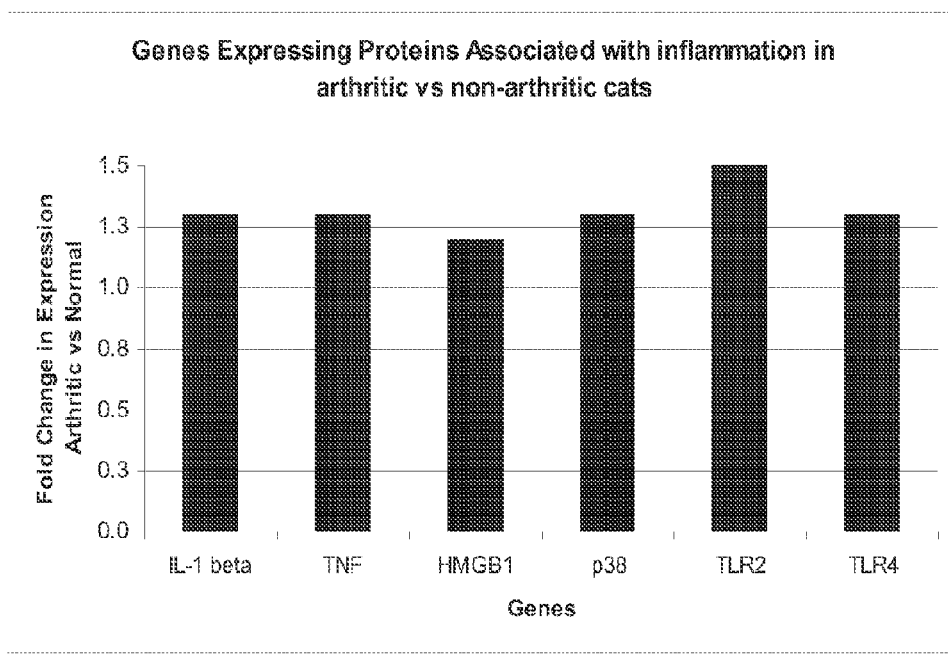
FIG. 3 depicts an increase in gene expression of various genes associated with inflammation in arthritic cats compared to non-arthritic cats.
Figure 15:
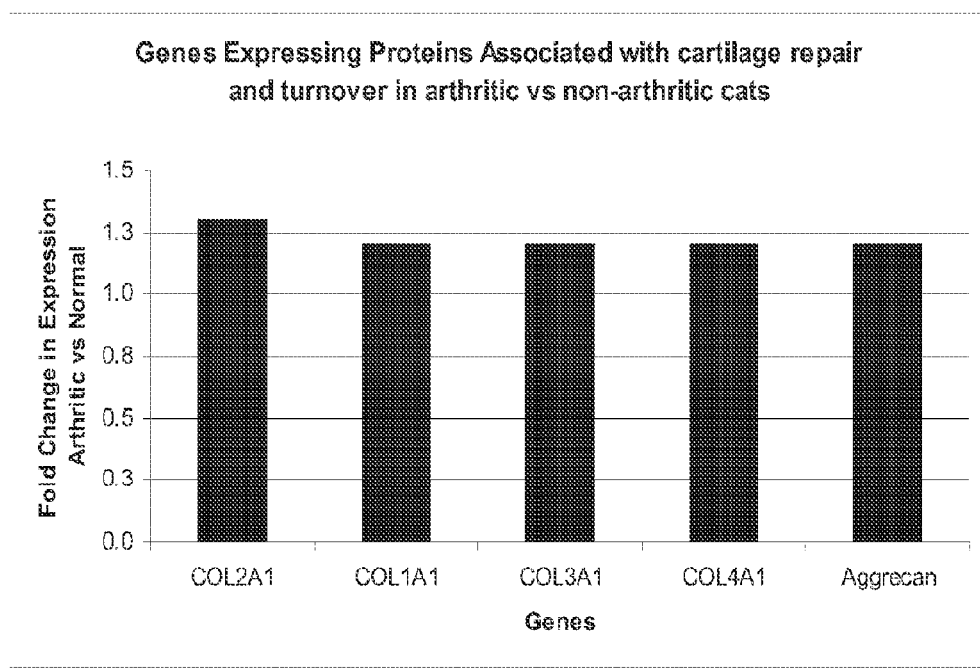
FIG. 15 depicts upregulation of various genes associated with cartilage repair in arthritic versus non-arthritic cats.

Gene expression profiling was determined in arthritic and non-arthritic cats and the results are reported in FIGS. 3 and 15. The genes found to be upregulated by greater than 1-fold in arthritic cats were the following: IL-1beta, TNF, HMGB1, p38, TLR2 and TLR4. These genes and their gene products are associated with inflammatory processes and would be considered as markers of abnormal musculoskeletal disorders, particularly osteoarthritis. In addition, the following genes were found to be up-regulated by greater than 1-fold in arthritic cats: COL2A1, COL1A1, COL3A1, COL4A1 and Aggrecan. These genes and their gene products are associated with cartilage degradation and would serve as markers of abnormal musculoskeletal disorders, particularly osteoarthritis.

The results from a study conducted in accordance with Example 6 indicates that gene expression can be used to differentiate between normal cats and cats with osteoarthritis. Differentially expressed genes associated with inflammation in arthritic cats appear on FIGS. 3 and 15. Thus, the identified genes may serve as biomarkers in cats for the inventions described herein and include the following genes:

IL-1 beta, TNF, HMGB1, p38, TLR2, TLR4, COL2A1, COL1A1, COL3A1, COL4A1 and Aggrecan.

Figure 16:
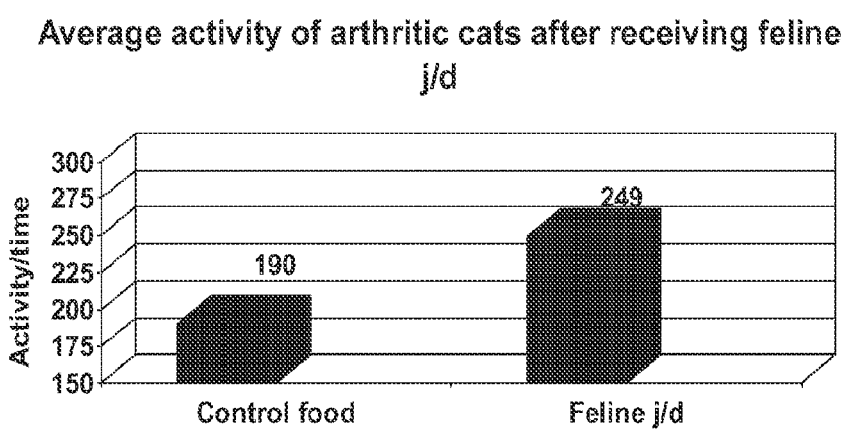
FIG. 16 depicts an increase in mobility of cats after receiving feline composition j/d.

Example 7: Average Activity of Arthritic Cats Following Administration of Feline Food Composition j/d Clinical data obtained from nutritional studies involving the arthritic and non-arthritic cats as described in Example 6 indicate that dietary intervention can affect and enhance the mobility of arthritic cats. Cats fed a diet of feline food composition j/d of the invention evidenced a statistically significant increase in activity over cats fed a control diet. The results of a clinical investigation are reported on FIG. 16. Based on observational data, cats feed the food composition j/d of the present invention showed greater than a 30% increase in movement signifying an improvement in the underlying symptomatology of osteoarthritis was achieved through administration of the test diet of the invention. A skilled worker can infer from the data presented in FIG. 16 that the cats had greater motility, less pain and inflammation as a result of the administration of the test diet food composition j/d.

Figure 17:
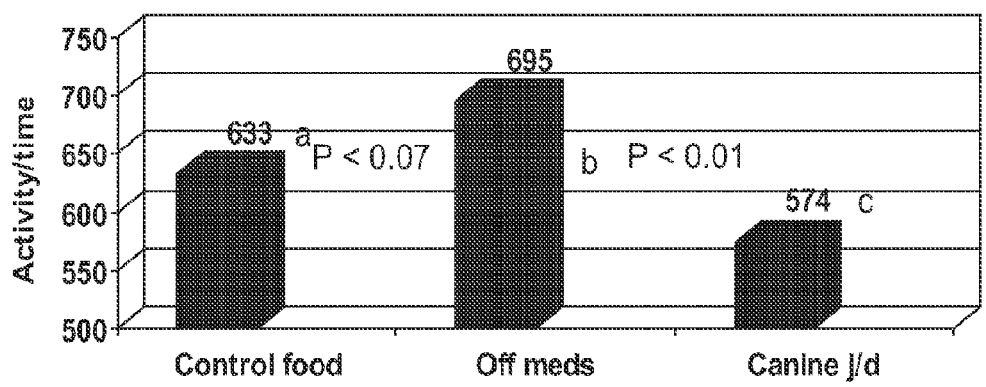
FIG. 17 depicts a reduction in nighttime activity of dogs indicating improved comfort in dogs administered canine food composition j/d

Example 8: Nighttime Activity in Dogs Following Administration of Composition j/d A clinical trial involving administration of canine food composition j/d of the present invention was conducted in dogs. Observations of nighttime activity of arthritic dogs fed food composition j/d were performed and recorded versus dogs fed a control food and in dogs receiving no medications. Measurements were made with ACTIWATCH® devices. These devices are actigraphy-based data loggers that record a digitally integrated measure of gross motor activity. Each device uses actigraphy principles to provide sleep schedule variability, sleep quantity and quality statistics and daytime activity patterns. The devices collect objective data relating to the animal's ambulatory environment. The results of this clinical trial demonstrated a significant reduction in nighttime activity of the arthritic dogs, thereby demonstrating that the dogs fed food composition j/d enjoyed greater relief and comfort from the underlying arthritic symptomatology including joint stiffness and pain. Data from this clinical trial is reported in FIG. 17.

Figure 5:
FIG. 5 depicts upregulation of gene C2C in arthritic dogs compared to normal dogs.
Figure 6:
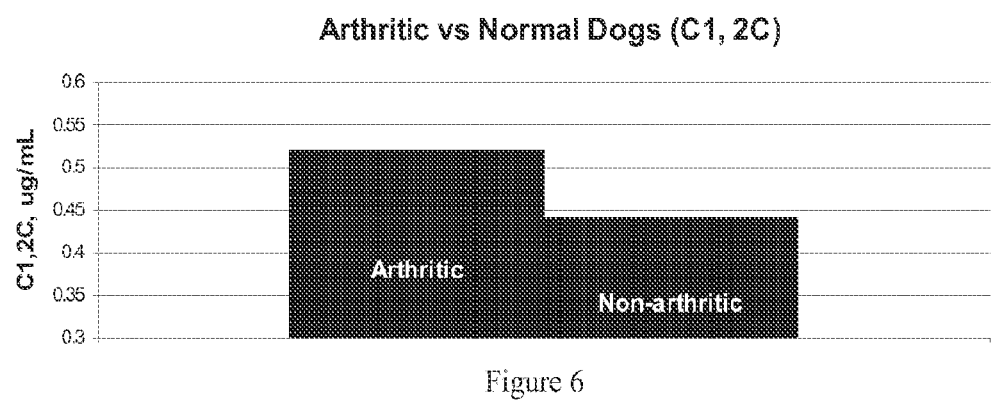
FIG. 6 depicts upregulation of gene C1,2C in arthritic dogs compared to non-arthritic dogs.
Figure 7:
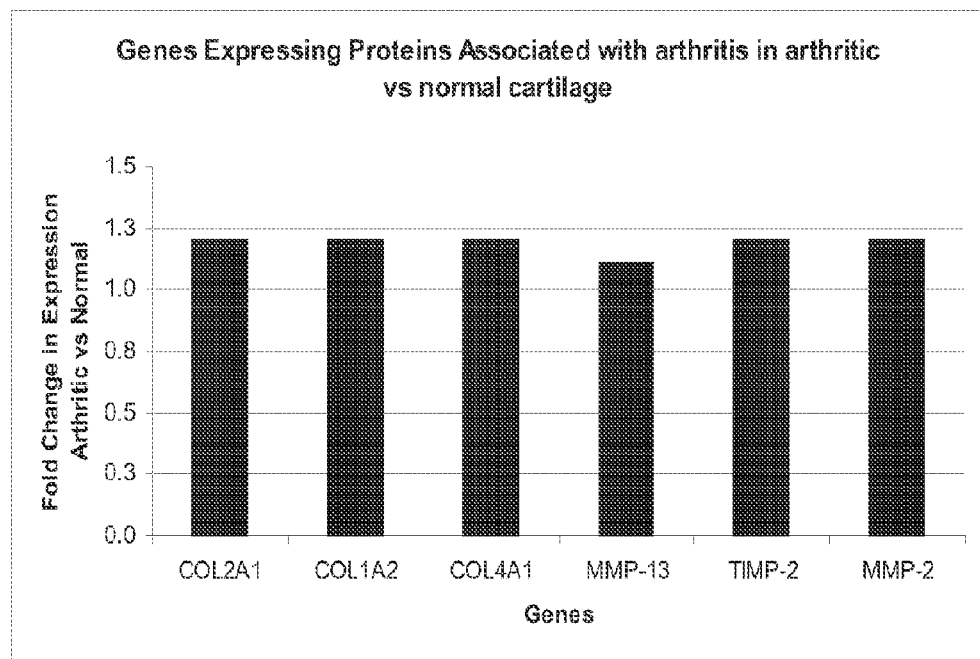
FIG. 7 depicts certain genes expressing proteins associated with arthritis in arthritic versus non-arthritic cartilage in dogs.
Figure 8:
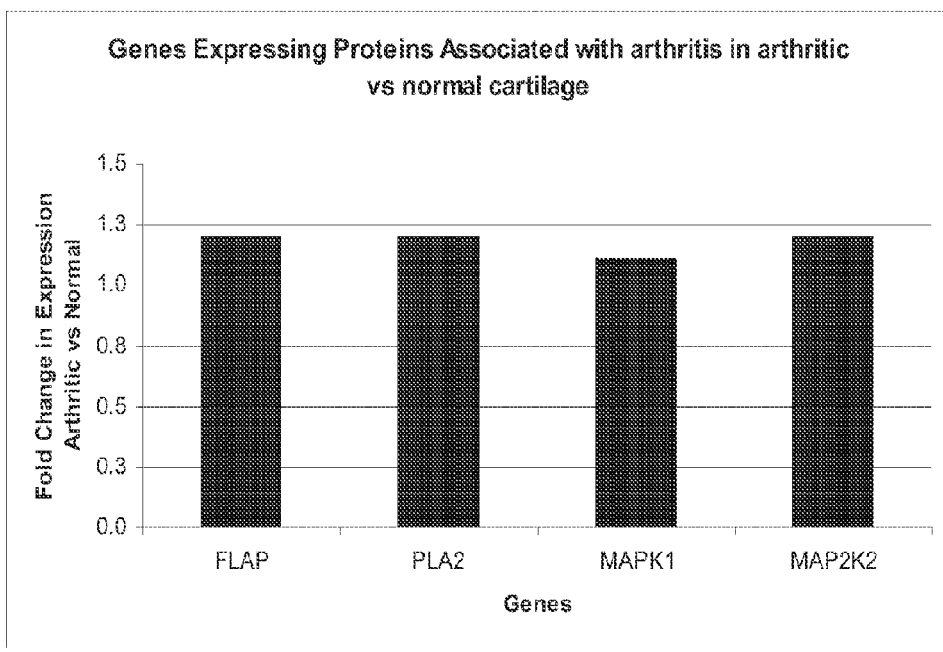
FIG. 8 depicts certain genes expressing proteins associated with arthritis in arthritic versus non-arthritic cartilage in dogs.
Figure 9:
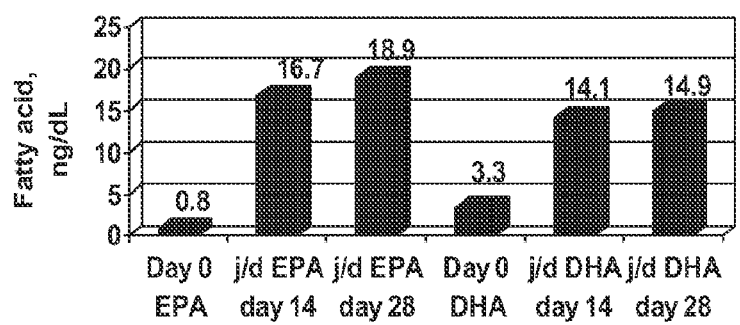
FIG. 9 depicts serum levels of EPA and DHA after feeding canine food composition j/d to dogs for 14 and 18 days, respectively.

Example 9: Protein Marker Levels in Dogs after Receiving Canine Food Composition j/d Baseline levels of two protein markers associated with cartilage degradation in dogs, C2C and C1,C2 were obtained in arthritic and non-arthritic dogs. Blood samples of the animals were drawn and tested by conventional means described in this specification. The results of the testing demonstrated that the gene products of these markers were elevated in arthritic dogs and could be used as markers to determine the effectiveness of dietary components upon gene expression. The baseline data is presented in FIGS. 5 and 6.

Figure 10:
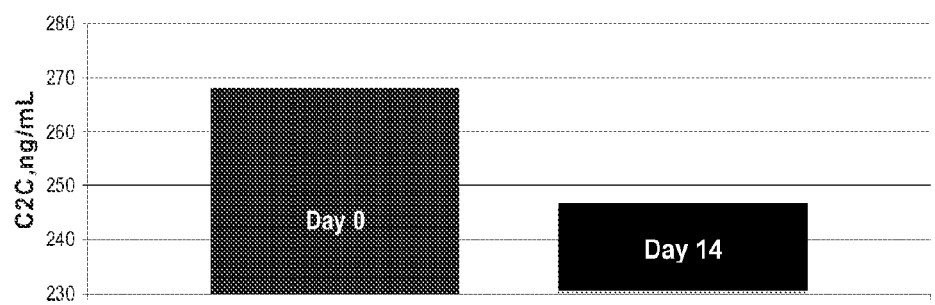
FIG. 10 depicts modulating expression of gene C2C after feeding dogs with canine composition j/d for a period of 14 days.
Figure 11:
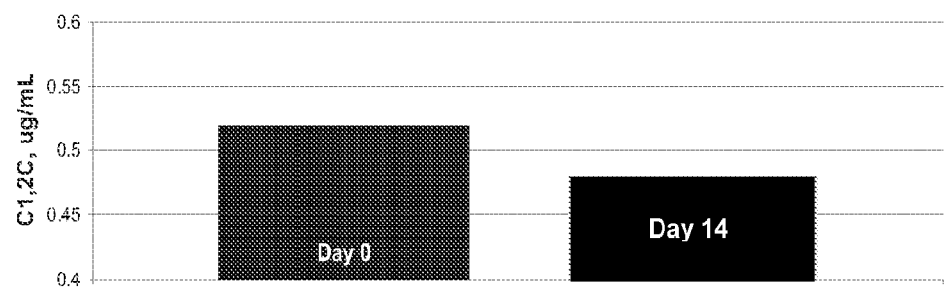
FIG. 11 depicts modulating expression of gene C1,2C after feeding dogs with canine composition j/d for a period of 14 days.
Figure 12:
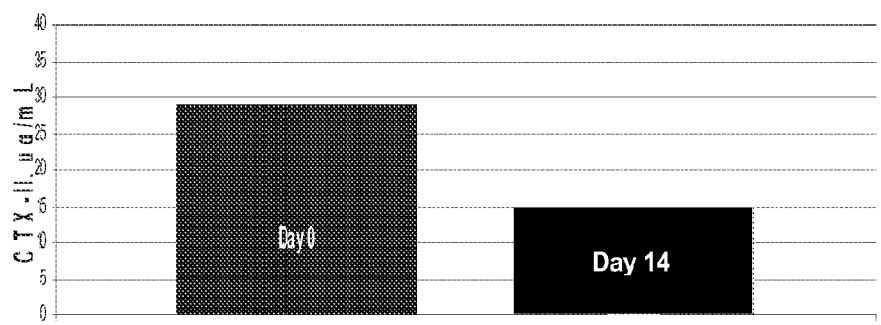
FIG. 12 depicts modulating expression of gene CTX-II after feeding dogs with composition j/d for a period of 14 days.
Figure 13:
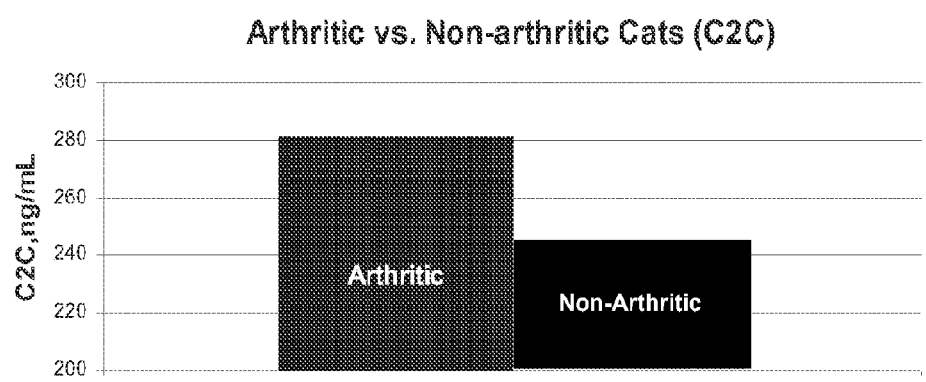
FIG. 13 depicts upregulation of gene C2C in arthritic versus non-arthritic cats.
Figure 14:
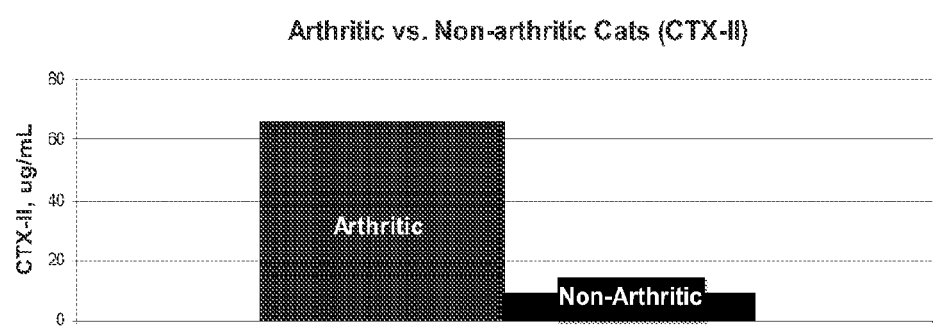
FIG. 14 depicts upregulation of gene CTX-II in arthritic cats versus non-arthritic cats.

Clinical data obtained from nutritional studies involving arthritic and non-arthritic dogs. Test dogs as described in this Example were fed a diet of the present invention, which is identified as food composition j/d on FIG. 4. Evaluations of the C2C and C1,C2 arthritic marker levels and the level of another protein marker known to be relevant to abnormal musculoskeletal joint disorders, namely Collagen CTX-II, were made. Data depicted on FIGS. 10, 11 and 12 present protein marker levels as determined in the blood of test and control animals. Dogs fed a diet of canine food composition j/d as set forth on FIG. 4 evidenced a statistically significant decrease in plasma C2C, C1,C2 and CTX-II levels as depicted on FIGS. 10, 11 and 12. A skilled worker will recognize that this biomarker data supports the clinical observation that dogs fed the dietary compositions of the invention, in particular, food composition j/d as demonstrated in this Example, exhibit an improvement in clinical symptomatology of the underlying disease process, in this case osteoarthritis, which correlates with the down-regulation of certain genes and the reduced expression of certain gene products which have been associated with cartilage degradation and local joint inflammatory conditions, including osteoarthritis.

Example 10: Gene Chip Analyses of Up- and Down-Regulated Canine Genes in Arthritic and Non-Arthritic Canines A commercially-available canine gene chip (Affymetrix GeneChip2) was used to evaluate baseline gene expression in two groups of dogs with and without arthritis, as determined in accordance with standard clinical diagnostic criteria known in the art. Gene chip analyses were performed using conventional methods and according to the manufacturer's instructions. Using the general expression profiling procedures of Example 1 and the analytical techniques outlined in other Examples set forth in this specification, gene expression profiling was performed to obtain a baseline comparison between the two groups to determine the underlying gene expression differences between non-arthritic dogs and dogs.

Following standard animal nutrition testing procedures familiar to one of ordinary skill in the art, arthritic and normal dogs were fed test diets comprising the food composition designated j/d and then changes in gene expression in the animals were analyzed using qRT-PCR.

The raw gene chip data is normalized using the Robust Multiarray Average (RMA) normalization algorithm (Irizarry, et al., Biostatistics 2003 Vol 4, Page 249-264) and is then subjected to statistical analysis using Support Vector Machine (SVM) algorithm (Partek Genomic Suite, Version 6) to determine the gene expression differences that can differentiate between arthritic and non-arthritic animals. Genes identifying arthritis biomarkers are selected based on p value cut off and fold change (FC).

The raw gene chip data is normalized using the Robust Multiarray Average (RMA) normalization algorithm (Irizarry, et al., Biostatistics 2003 Vol 4, Page 249-264) and is then subjected to statistical analysis using Support Vector Machine (SVM) algorithm (Partek Genomic Suite, Version 6) to determine the gene expression differences that can differentiate between arthritic and non-arthritic animals. Genes identifying OA biomarkers are selected based on p value cut off and fold change (FC).

The results from these studies indicate that gene expression can be used to differentiate between normal dogs and dogs with arthritis. Differentially expressed genes associated with inflammation in arthritic dogs appear on FIGS. 1, 2, 7 and 8. Without limiting the generality of the disclosures set forth in this application, the genes presented in FIGS. 1, 2, 7 and 8 may serve as biomarkers for the inventions described herein and include Annexin A1, Cathepsin D, Cathepsin F, Cathepsin S, RELA, HMGB1, IL-15, IL-17 receptor, TLR4,

COL2A1, COL1A1, COL4A1, MMP-13, TIMP-2, MMP-2, FLAP, PLA2, MAPK1, MAPK2.

Example 11: Gene Chip Analyses of Up- and Down-Regulated Canine Genes in Arthritic and Non-Arthritic Canines Fed a Diet of Food Composition j/d A commercially-available canine gene chip (Affymetrix GeneChip2) was used to evaluate gene expression in two groups of dogs with and without osteoarthritis. A total of 30 arthritic dogs and 31 non-arthritic dogs were studied. Gene chip analyses were performed using conventional methods and according to the manufacturer's instructions. Using the general expression profiling procedures of Example 1 and the analytical techniques outlined in other Examples set forth in this specification, gene expression profiling was performed. The first group of 30 test animals was determined to be arthritic in accordance with clinical diagnostic procedures that are well known in the art. The second group of canines was considered to be non-arthritic in accordance with the same clinical diagnostic criteria. Following standard animal nutrition testing procedures familiar to one of ordinary skill in the art, arthritic and normal dogs were fed test diets comprising the food composition designated j/d and then changes in gene expression in the animals were analyzed using qRT-PCR.

Following standard animal nutrition testing procedures familiar to one of skill in the art, arthritic and normal dogs were fed the test diet designated j/d and then changes in gene expression in the animals were analyzed using qRT-PCR.

With regard to q RT-PCR, Taqman probe technology is used and all analyses are carried out using an Applied Biosystems 7500 real-time PCR machine. The data is analyzed using the sequence detection software package version 1.2.2. provided by the manufacturer.

Using tissue samples prepared as described in the Examples, a commercially-available canine gene chip (Affymetrix GeneChip2) was used to evaluate gene expression in dogs with and without arthritis. The raw gene chip data is normalized using the Robust Multiarray Average (RMA) normalization algorithm (Irizarry, et al., Biostatistics 2003 Vol 4, Page 249-264) and is then subjected to statistical analysis using Support Vector Machine (SVM) algorithm (Partek Genomic Suite, Version 6) to determine the gene expression differences that can differentiate between arthritic and non-arthritic animals. Genes identifying arthritis and inflammation biomarkers are selected based on p value cut off and fold change (FC).

The data from this Example is set forth in Table 3. The data comprises 2383 records when a fold change cut-off of 1.1 is employed, a p-value cut-off of 0.05 and a Q-value cut-off of 0.3. Using these analytical criteria, a fold change of greater than 1 implies that the probes are UP regulated in samples taken from the arthritic dog group. The data presented in Table 3 identifies in the first column the unique Affymetrix probe identification number, and respectively thereafter the p-values, q-values, fold change, 1/fold change values, Top BLAST annotation, match percentage, human accession number, top hit accession number, gene symbol and gene description. A skilled worker will deduce from this data the following information using only ordinary experimental analysis: fold change cut-off criteria, the genes of interest that have been up or down regulated and the identification of such genes by BLAST annotation, related human accession numbers and the sequence for each such identified gene as well as the corresponding gene products and sequences of such gene products based on the information available from the manufacturer as well as from gene sequence databases that are readily available to the skilled artisan. In addition, sequences for the unique probes utilized in the Affymetrix arrays are publicly available by reference to published sources of the manufacturer. Similarly, published sequence information and identification of the respective probes utilized on versions 1 and 2 of the Affymetrix chips are readily and publicly available from the manufacturer as well as comparison of the probe sets to each other. From this data a skilled worked can identify and utilize such gene expression data, the identified genes that have been dysregulated and their corresponding gene products in the practice of manufacturing and using compositions and article of manufacture of the present invention as well as in practicing methods of manufacturing and using inventions taught in this specification. Without intending to limit the extent of the inventions disclosed and claimed in this application, certain genes and gene products of interest may be identified as highly pertinent to arthritic conditions in dogs and cats. These and other genes and gene products taught in the data set forth in Table 3 may be inferred as having a beneficial effect upon the underlying abnormal musculoskeletal joint disorder, in particular arthritic conditions, experienced by dogs and cats when the animals are fed the compositions of the invention, in particular the food compositions designated j/d, which modulates the genes of interest set forth in Table 3.

Lengthy table referenced here

US09629382-20170425-T00001

Please refer to the end of the specification for access instructions.

Lengthy table referenced here

US09629382-20170425-T00002

Please refer to the end of the specification for access instructions.

Lengthy table referenced here

US09629382-20170425-T00003

Please refer to the end of the specification for access instructions.

LENGTHY TABLES

The patent contains a lengthy table section. A copy of the table is available in electronic form from the USPTO web site (http://seqdata.uspto.gov/?pageRequest=docDetail&DocID=US09629382B2). An electronic copy of the table will also be available from the USPTO upon request and payment of the fee set forth in 37 CFR 1.19(b)(3).

What is claimed is:

1. A food composition for a companion animal comprising,
   at least one omega-3 fatty acid, wherein the omega-3 fatty acid is selected from the group consisting of alpha-linoleic acid (ALA), docosahexanoic acid (DHA) and eicosapentaenoic acid (EPA), and wherein the ALA is present in amount of about 10-100 mg/kg/day, the DHA is present in an amount of about 1-30 mg/kg/day, and/or EPA is present in an amount of about 1-30 mg/kg/day;
   at least one glycosaminoglycan;
   at least one amino sugar;
   at least one antioxidant;
   carnitine or acetylcarnitine; and
   one or more omega-6 fatty acids comprising arachidonic acid (ARA), wherein the ARA is present in an amount of about 5-50 mg/kg/day;
   wherein the composition is formulated for oral administration,
   wherein the composition is a nutritionally balanced canine food composition,
   wherein the companion animal is a canine, and
   wherein the at least one antioxidant is selected from the group consisting of tocotrienols, glutathione, lipoic acid, melatonin, and beta-carotene.

2. The composition of claim 1, wherein the glycosaminoglycan is selected from the group consisting of chondroitin sulfate, dermatan sulfate, keratan sulfate, heparin, heparan sulfate and hyaluronan.

3. The composition of claim 1, wherein the amino sugar is selected from the group consisting of galactosamine, glucosamine, sialic acid and N-acetylglucosamine.

4. The composition of claim 1 further comprising at least one dietary mineral.

5. The composition of claim 4, wherein the dietary mineral is selected from the group consisting of Calcium, Chloride, Magnesium, Phosphorus, Potassium, Sodium, Cobalt, Copper, Fluorine, Iodine, Iron, Manganese, Molybdenum, Nickel, Selenium, Sulfur, Zinc and Vanadium.

6. The composition of claim 5, further comprising at least one essential amino acid.

* * * * *